(12) United States Patent
Miller et al.

(10) Patent No.: US 6,458,249 B2
(45) Date of Patent: *Oct. 1, 2002

(54) PROCESS FOR PURIFYING PERFLUORINATED PRODUCTS

(75) Inventors: Ralph Newton Miller, Newark, DE (US); Chien-Ping Chai Kao, Newark, DE (US); Barry Asher Mahler, Glen Mills, PA (US)

(73) Assignee: E. I. du Pont de Nemours and Company, Wilmington, DE (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/189,322

(22) Filed: Nov. 9, 1998

Related U.S. Application Data

(60) Provisional application No. 60/064,993, filed on Nov. 10, 1997, and provisional application No. 60/086,146, filed on May 20, 1998.

(51) Int. Cl.[7] ............................. B01D 3/34; C01B 21/04; C07C 17/386
(52) U.S. Cl. ............................. 203/51; 203/49; 203/57; 203/67; 203/68; 203/70; 203/71; 423/406; 570/178
(58) Field of Search ............................. 423/406; 203/71, 203/51, 67, 34, 100, 31, 70, 57, 52, 68, 49; 570/177, 178

(56) References Cited

U.S. PATENT DOCUMENTS

| | | | | |
|---|---|---|---|---|
| 3,927,103 A | * | 12/1975 | Koshar et al. | 548/251 |
| 4,933,158 A | * | 6/1990 | Aritsuka et al. | 423/406 |
| 4,948,571 A | * | 8/1990 | Harada et al. | 423/406 |
| 4,975,259 A | * | 12/1990 | Hyakutake et al. | 423/406 |
| 4,980,144 A | * | 12/1990 | Koto et al. | 423/406 |
| 5,069,887 A | | 12/1991 | Suenaga et al. | 423/240 |
| 5,626,023 A | | 5/1997 | Fisher et al. | 62/625 |
| 5,771,713 A | | 6/1998 | Fisher | 62/625 |
| 6,187,077 B1 | * | 2/2001 | Li | 95/47 |

FOREIGN PATENT DOCUMENTS

| | | | | |
|---|---|---|---|---|
| EP | 0 583 551 A1 | 2/1994 | | C07C/17/38 |
| JP | 63151608 | 6/1988 | | C01B/21/083 |
| JP | 870138972 | 12/1988 | | |

* cited by examiner

*Primary Examiner*—Virginia Manoharan
(74) *Attorney, Agent, or Firm*—J. E. Shipley

(57) ABSTRACT

Nitrogen trifluoride ($NF_3$) containing less than 10 parts-per-million molar impurities, e.g., tetrafluoromethane (PFC-14), is disclosed. Azeotropic and extractive distillation processes using entraining agents for separating $NF_3$ and PFC-14 from each other and from mixtures with other electronics industry materials are disclosed.

23 Claims, 7 Drawing Sheets

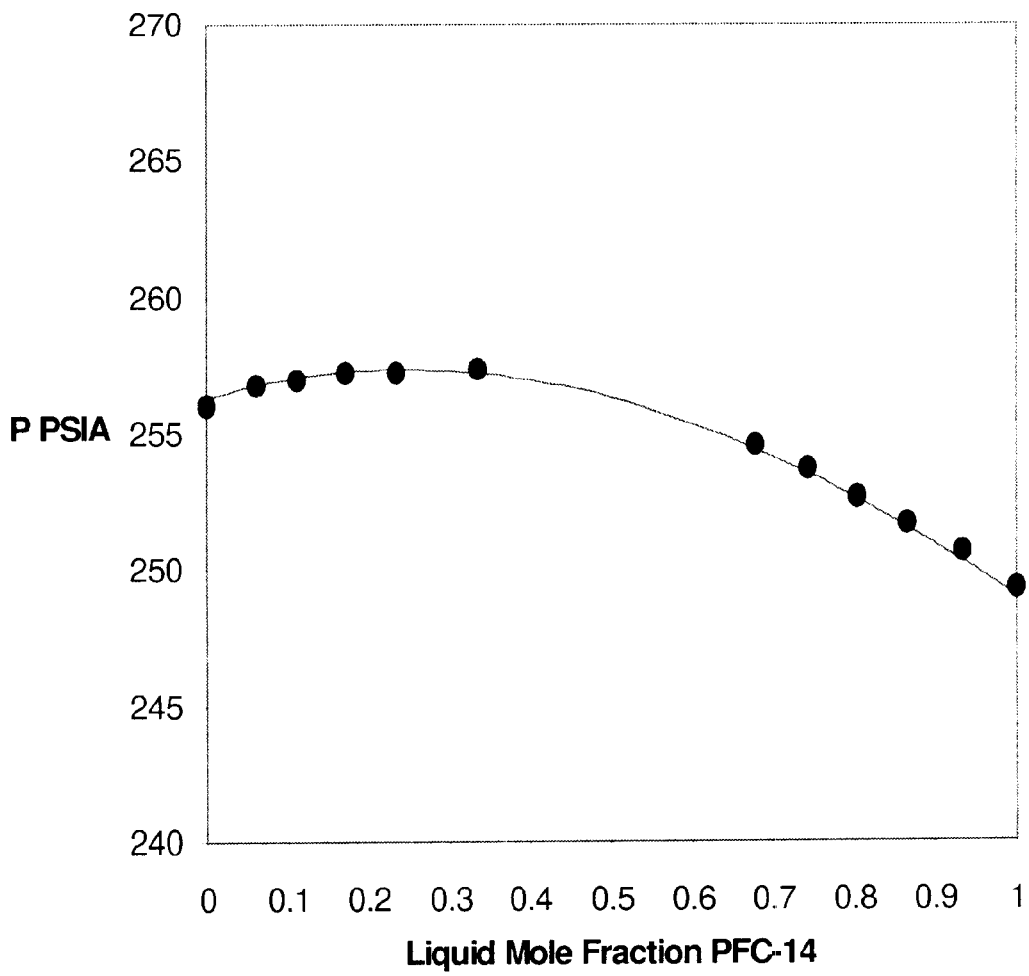

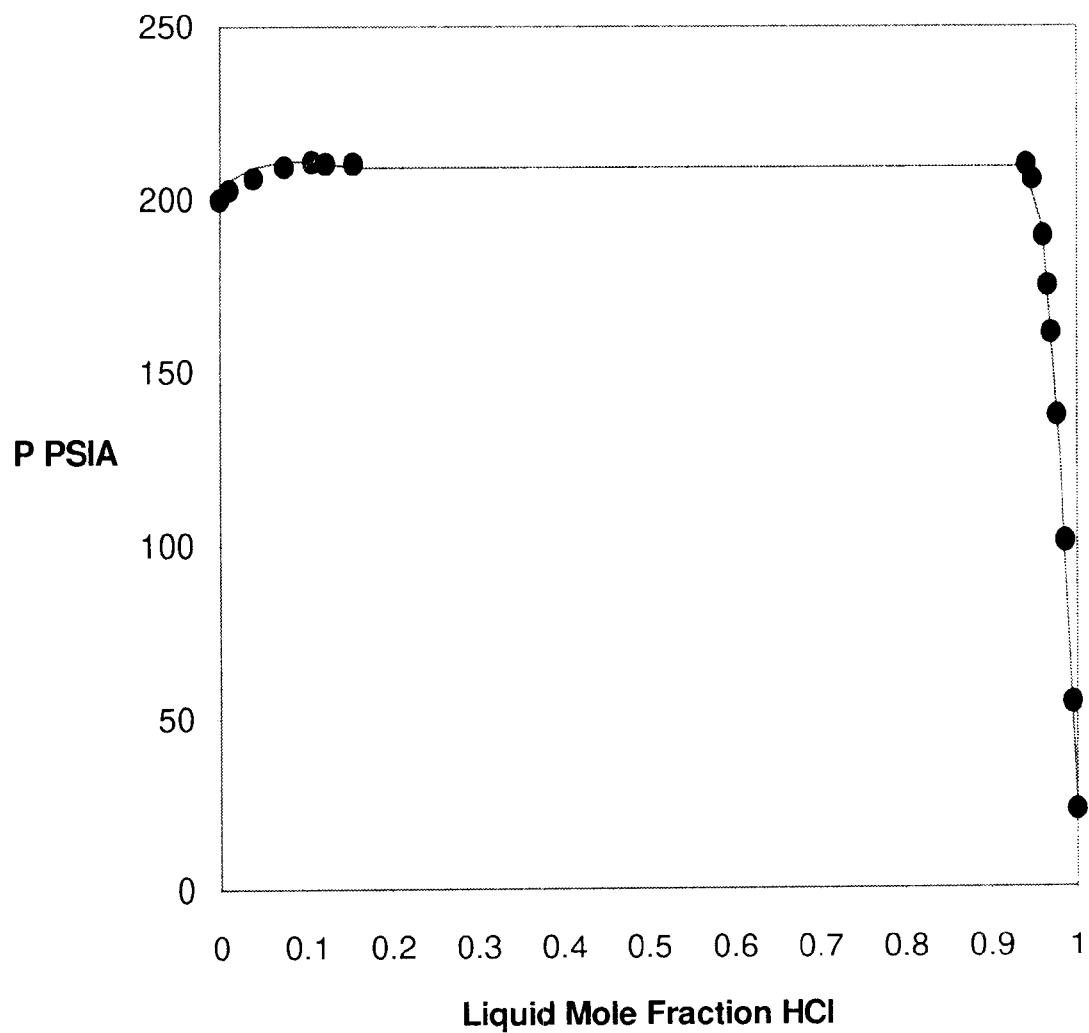

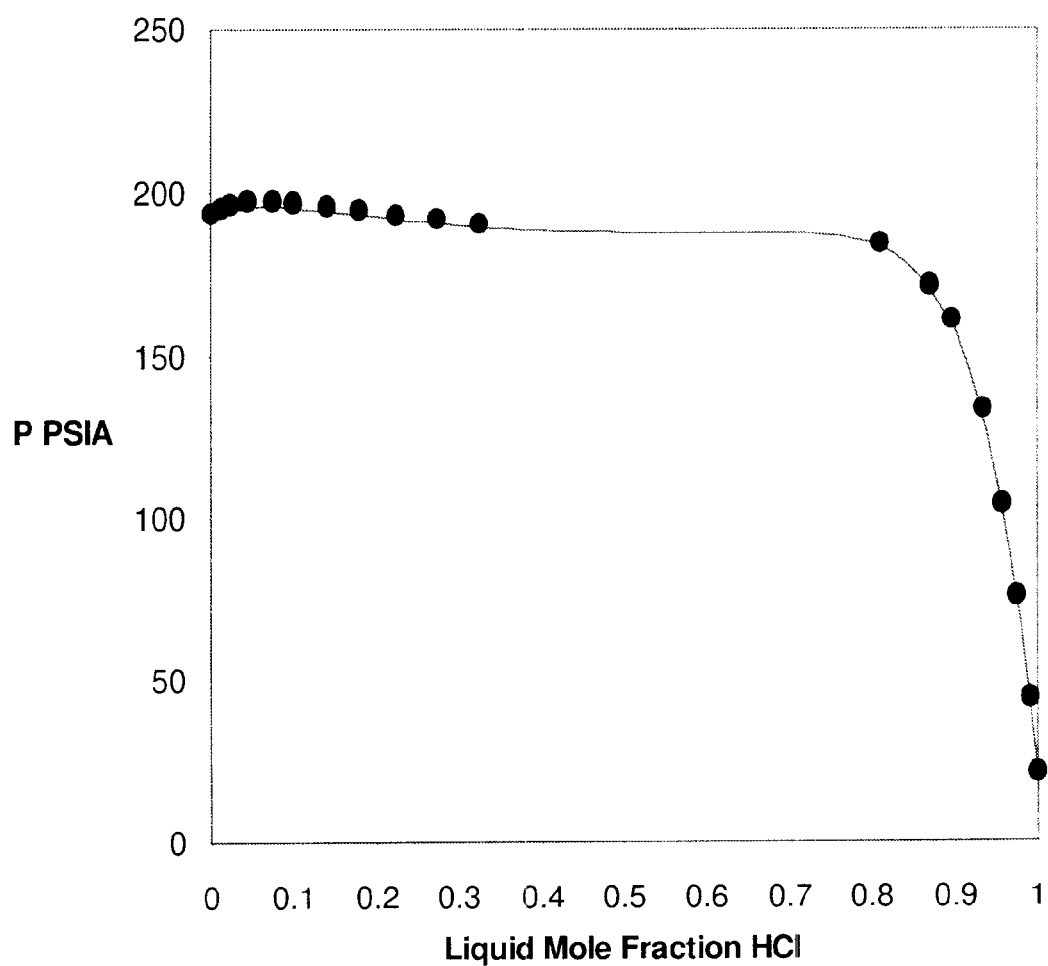

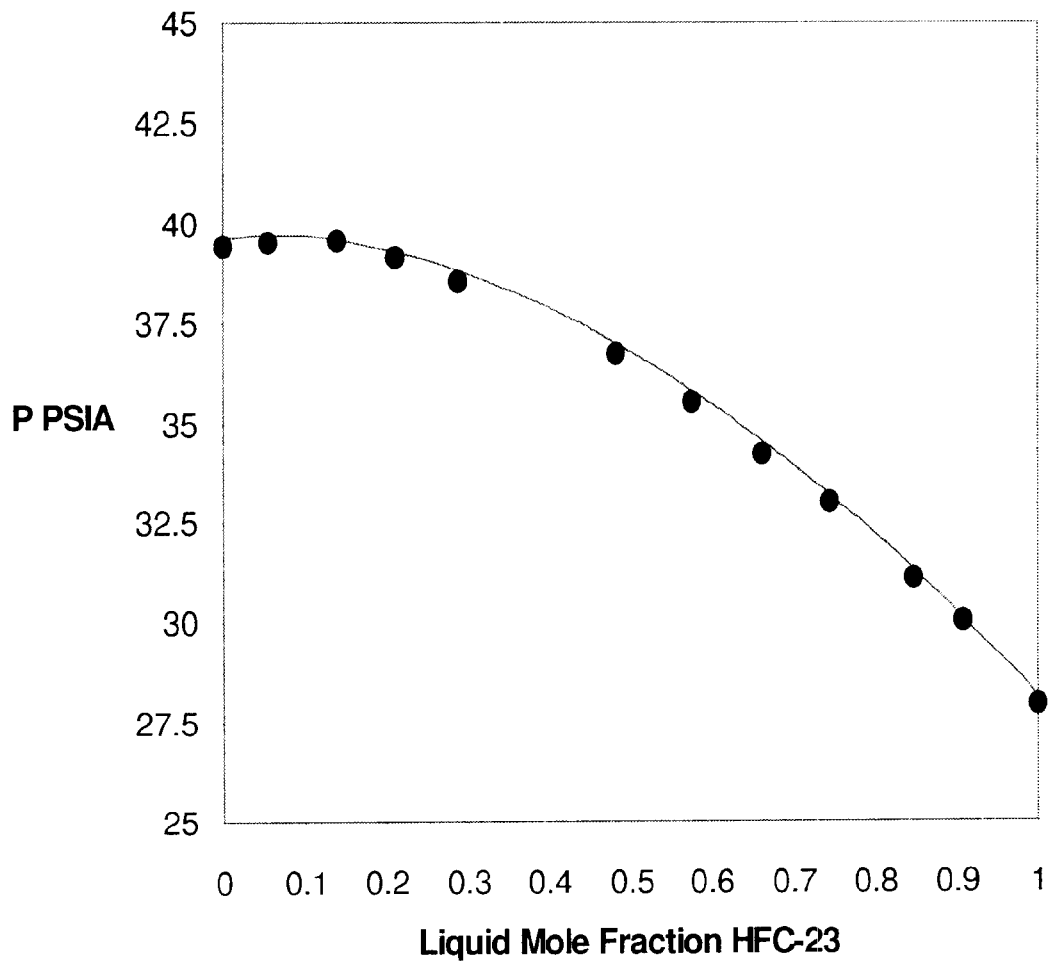

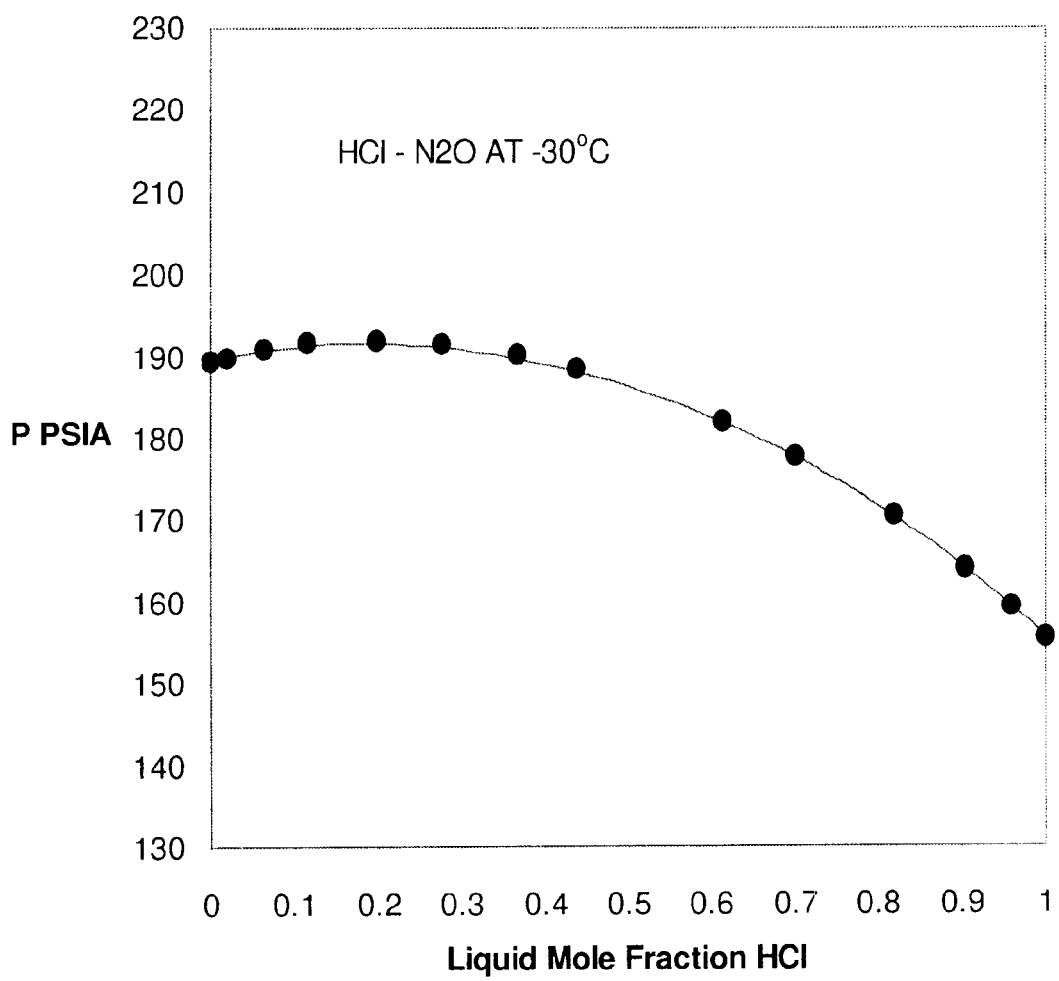

PROCESS FOR PURIFYING PERFLUORINATED PRODUCTS

CROSS REFERENCE TO RELATED APPLICATIONS

This application claims the priority benefit of U.S. Provisional Application No. 60/064,993, filed Nov. 10, 1997, and U.S. Provisional Application No. 60/086,146, filed May 20, 1998.

FIELD OF THE INVENTION

The present invention relates to processes for separating and purifying perfluorinated products from a starting mixture containing a variety of compounds by using azeotropic and extractive distillation processes, such that perfluorinated products of high purity are obtained.

BACKGROUND OF THE INVENTION

Various gaseous fluorine-containing compounds are utilized in manufacturing processes that plasma-etch silicon-type materials in order to fabricate semiconductor devices. A major use of tetrafluoromethane ($CF_4$ or PFC-14) is for plasma etching during semiconductor device fabrication. Plasma etchants interact with the surface of the integrated circuit wafer, modifying it so as to lay down the electrical pathways and providing for the surface functionalities that define the integrated surface. A major use of nitrogen trifluoride ($NF_3$) is as a "chemical vapor deposition" (CVD) chamber cleaning gas in semiconductor device manufacture. CVD chamber cleaning gases are used to form plasmas which interact with the internal surfaces of semiconductor fabrication equipment to remove the various deposits that accumulate over time.

Perfluorinated chemicals such as PFC-14 and $NF_3$ that are used in semiconductor manufacturing applications as etchant or cleaning gases are more commonly referred to as "electronic gases". Electronic gases having high purity are critical for such semiconductor device manufacture applications. It has been found that even very small amounts of impurities in these gases that enter semiconductor device manufacturing tools can result in wide line width and thus less information per device. Moreover, the presence of these impurities, including but not limited to particulates, metals, moisture, and other halocarbons in the plasma etchant or cleaning gases, even when only present in the part-per-million level, increases the defect rate in the production of these high-density integrated circuits. As a result, there has been increasing demand for higher purity etchant and cleaning gases, and an increasing market value for the materials having the required purity. Identification of offending components and methods for their removal consequently represents a significant aspect of preparing the fluorine-containing compounds for these applications.

These etchant and cleaning gases are not fully consumed by semiconductor manufacturing processes, but typically exit the integrated circuit fabrication equipment in finite concentrations. These fabrication equipment exhaust streams not only contain varying amounts of the unreacted perfluorinated etchant and cleaning gases, but may also contain a variety of reaction products and air components, which include but are not limited to hydrogen fluoride (HF), tetrafluoroethylene ($C_2F_4$ or PFC-1114), methyl fluoride ($CH_3F$ or HFC-41), trifluoromethane ($CHF_3$ or HFC-23), chlorotrifluoromethane ($CClF_3$ or CFC-13), nitrogen, oxygen, carbon dioxide, water, methane, ethane, propane and nitrous oxide ($N_2O$). A variety of other fluorinated compounds are also used in semiconductor manufacturing applications, including hexafluoroethane ($C_2F_6$ or PFC-116), octafluorocyclobutane (cyclic $C_4F_8$ or PFC-C318), octafluoropropane ($C_3F_8$ or PFC-218), sulfur hexafluoride ($SF_6$), pentafluoroethane ($C_2HF_5$ or HFC-125), trifluoromethane ($CHF_3$ or HFC-23), tetrafluoroethane ($C_2H_2F_4$, or HFC-134a or HFC-134) and difluoromethane ($CH_2F_2$ or HFC-32), and the exhaust streams coming off these processes are frequently combined with the exhaust streams from the PFC-14 and $NF_3$ processes. The resulting combined exhaust stream consequently may contain a wide range of compounds and concentrations.

Considerable effort is underway to develop ways and means to capture the fluorinated compounds present in such equipment exhaust streams and to develop options for their disposition. A preferred disposition option is to repurify certain of the fluorinated components from these streams for reuse. Separation of several of these valuable fluorinated compounds is made difficult due to the variety of fluorinated compounds that might be present in the combined exhaust gas stream from any given manufacturing site, and due to non-ideal interactions that exist between several of these compounds. For example, several of these compounds form azeotropic or azeotrope-like compositions with other compounds in these streams, making separation by conventional distillation at least difficult, if not impossible.

The present invention provides compositions and distillation processes for removing fluorinated impurities from an impure stream comprising at least one of PFC-14 and $NF_3$ so as to produce a purified PFC-14 and/or $NF_3$ product. The present processes are simple to carry out and are effective for obtaining either of these two compounds in high purity and with high degrees of recovery.

SUMMARY OF THE INVENTION

The present invention comprises $NF_3$ substantially free of impurities, containing less than 10 parts-per-million molar of impurities. The present invention further comprises $NF_3$ containing less than 10 parts-per-million molar PFC-14.

The present invention further comprises azeotropic compositions consisting essentially of: $NF_3$ and PFC-14; hydrogen chloride and PFC-14; $NF_3$ and hydrogen chloride; nitrous oxide and trifluoromethane; and nitrous oxide and hydrogen chloride.

The present invention further comprises a process for separating at least one of PFC-14 and $NF_3$ from a first mixture comprising PFC-14, $NF_3$, and optionally other fluorinated compounds, comprising the steps of:

contacting at least one entraining agent with the first mixture to form a second mixture, distilling the second mixture, and recovering at least one of PFC-14 and $NF_3$ that is substantially free of at least one of the other fluorinated components of the first mixture.

BRIEF DESCRIPTION OF THE DRAWINGS

FIG. 3 is a graphical representation of an azeotropic and azeotrope-like composition consisting essentially of PFC-14 and $NF_3$ at a temperature of about −70° C.

FIG. 4 is a graphical representation of an azeotropic and azeotrope-like composition consisting essentially of PFC-14 and HCl at a temperature of about −76° C.

FIG. 5 is a graphical representation of an azeotropic and azeotrope-like composition consisting essentially of $NF_3$ and HCl at a temperature of about −78° C.

FIG. 6 is a graphical representation of an azeotropic and azeotrope-like composition consisting essentially of $N_2O$ and HFC-23 at a temperature of about −70° C.

FIG. 7 is a graphical representation of an azeotropic and azeotrope-like composition consisting essentially of HCl and $N_2O$ at a temperature of about −30° C.

DETAILED DESCRIPTION

Figure 1:
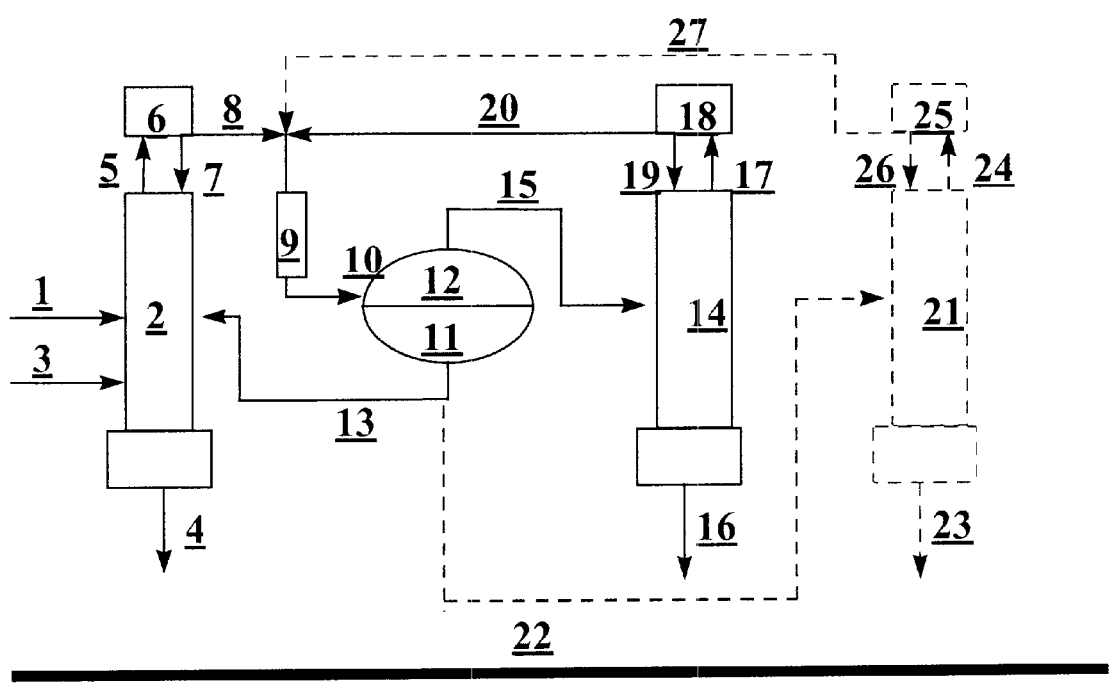
FIG. 1 is a schematic diagram of a distillation system that can be used for practicing an aspect of the present process.

PFC-14 and $NF_3$, in their separate and pure states, exhibit properties that are valued for integrated circuit manufacturing and are typically used in a variety of the related manufacturing steps. The desire for greater precision and consistency of the effect such compounds have during integrated circuit manufacture has made extremely high purities critical for such applications. The presence of any other compounds in the PFC-14 or $NF_3$ is objectionable for most of the intended uses. It should be recognized that any one of PFC-14 and $NF_3$ might in themselves be considered an impurity if present in the product stream of the other. For example, even a 1 parts-per-million-molar concentration of PFC-14 would be considered an impurity in $NF_3$ where that $NF_3$ is to be sold as a cleaning agent product. Similarly, even a 1 parts-per-million-molar concentration of $NF_3$ would be considered an impurity in PFC-14 where that PFC-14 is to be sold as an etchant product. Processes that allow for manufacture of PFC-14 or $NF_3$ products having purities that approach 99.999 molar percent purity are desirable, but processes that provide at least 99.9999 molar percent purity for electronic gas applications are preferred. Analytical methods for gauging such low concentrations of impurities in PFC-14 and $NF_3$ products are available. For example, methods for analyzing low concentrations of PFC-14 and other impurities in an $NF_3$ product is disclosed in the 1995 SEMI standards, pages 149–153, SEMI C3.39.91-Standard for Nitrogen Trifluoride. Alternately, techniques for analyzing the concentration of PFC-14 and other impurities at low concentrations in PFC-116, but which may also be applied to analysis of $NF_3$ and PFC-14 products, are disclosed in "Examining Purification and Certification Strategies for High-Purity $C_2F_6$ Process Gas", Micro Magazine, April 1998, page 35. The disclosure of the previous two references is hereby incorporated by reference.

Conventional processes for manufacturing $NF_3$ often produce PFC-14 as a component in the $NF_3$ product stream. Because conventional processes are not able to separate the PFC-14 from the $NF_3$ product, $NF_3$ products containing less than about 10 ppm-molar PFC-14 are not available in spite of the desirability of lower concentrations of PFC-14 in said $NF_3$ product.

Furthermore, during their use in integrated circuit manufacturing processes, neither the PFC-14 nor $NF_3$ electronic gases are completely consumed, and at least some amounts of these compounds remain in the manufacturing process equipment exhaust stream. This exhaust stream may contain a variety of additional impurities such as byproduct hydrogen chloride (HCl), hydrogen fluoride (HF), and a variety of fluorinated compounds, among others. In a typical manufacturing facility the exhaust streams from the various PFC-14 and $NF_3$ equipment are mixed not only with each other, but with the exhaust streams from equipment employing a variety of other fluorocarbon chemicals. Typically, this results in a stream containing a wide range of PFC-14, $NF_3$, and other fluorinated impurities in a wide range of concentrations. Typically this exhaust stream also contains relatively high volume concentrations, typically greater than 50 volume %, of inert carrier gases such as air, helium or nitrogen.

Concerns over possible environmental impact of such materials and the high value-in-use of these materials has prompted a search for methods of recovering PFC-14 or $NF_3$ from said exhaust streams of such processes. Conventional methods of recovering the components from such streams typically involve water washing the exhaust stream to remove the HF and HCl, then drying the stream using a variety of methods. Conventional methods for separating and recovering the fluorinated compounds from the large concentrations of inert carrier gases include use of semi-permeable membranes or adsorption of the fluorinated compounds into liquid solvents. However, a wide range of fluorinated organic and inorganic compounds typically still remain in the captured stream after such processing steps, making any PFC-14 or $NF_3$ contained within unsuitable for reuse as electronic gases.

The ability to separate and recover a $NF_3$ product that is substantially free of PFC-14 and other fluorinated impurities, particularly where the PFC-14 concentration in said $NF_3$ product is preferably less than 3, more preferably less than 1 ppm-molar, is of considerable commercial interest. The ability to separate and recover a PFC-14 product that is substantially free of fluorinated impurities is also of considerable commercial interest.

Many of the fluorinated compounds used or that are produced in semiconductor process operations are extremely close-boiling in their separated and pure states or otherwise exhibit non-ideal behavior such that their relative volatility approaches or even becomes 1.0 compared to any one of PFC-14 or $NF_3$. Compounds whose relative volatilities approach or equal 1.0 compared to PFC-14 or $NF_3$ make their separation from said PFC-14 or $NF_3$ by conventional distillation difficult. Separation of such mixtures is particularly problematic where it is desired that the recovered PFC-14 or $NF_3$ product be substantially free of other fluorinated compounds and where the PFC-14 or $NF_3$ product needs to be recovered from a first mixture with high recovery efficiency.

The present inventors have found that PFC-14 and $NF_3$ may be separated from a variety of fluorinated compounds and each other such that said PFC-14 or $NF_3$ may be recovered substantially free of other fluorinated compounds with high recovery efficiency of said PFC-14 or $NF_3$, and such that the separation is effected in an economical manner, by distilling a mixture comprising at least one of PFC-14 and $NF_3$ in the presence of an entraining agent that interacts in a non-ideal manner with the mixture. Entraining agents act in a manner so as to increase or decrease the volatility of the PFC-14 or $NF_3$ relative to a fluorinated impurity. These thus allow a PFC-14 or $NF_3$ product that is substantially free of fluorinated impurities to be separated and recovered from the initial mixture comprising PFC-14 or $NF_3$ by distillation.

In one aspect of this invention, an effective amount of an entraining agent is fed to a distillation column at a point equal to, or higher than, that at which the PFC-14 or $NF_3$ containing mixture is being fed. The entraining agent acts in a non-ideal manner with at least one of the PFC-14, $NF_3$, or their respective fluorinated impurities such that the relative volatility between the desired PFC-14 or $NF_3$ product and their respective fluorinated impurities is increased. By distilling the mixture, the fluorinated impurity may be separated from the desired PFC-14 or $NF_3$ product.

By effective amount of entraining agent is meant an amount of at least one entraining agent which, in the presence of a desired product and fluorinated impurity, causes the volatility of the fluorinated impurity to increase or decrease relative to the desired product sufficiently to allow separation by distillation of the impurity from the desired product. Further, by effective amount of entraining agent is meant an amount which, in the presence of a desired product and fluorinated impurity, results in the formation of a lower- or higher-boiling azeotropic or azeotrope-like composition or otherwise causes the volatility of the fluorinated impurity to increase or decrease relative to the desired product sufficiently to allow separation by distillation of the impurity from the desired product. This definition includes where the effective amount may vary depending on the pressure applied to the composition so long as the azeotrope or azeotrope-like compositions or changes in relative volatility continue to exist.

In one embodiment of the present invention, an effective amount of entraining agent is added to the PFC-14 or $NF_3$ containing mixture and the resulting mixture distilled under conditions such that azeotropic or azeotrope-like compositions are formed. The entraining agent acts in a non-ideal manner with at least one of the PFC-14, $NF_3$, or their respective fluorinated impurities such that the relative volatility between the desired PFC-14 or $NF_3$ product and their respective impurities is increased. By distilling the mixture, the fluorinated impurity may be separated from the desired PFC-14 or $NF_3$ product.

It is also recognized in the art that when the relative volatility of a system, for example, a mixture comprising any one of PFC-14 and $NF_3$ and at least one other compound approaches 1.0, that is for example when the relative volatility is 0.98 or 1.02, such defines the system as forming an azeotrope-like composition. When the relative volatility is equal to 1.0, such defines the system as forming an azeotrope.

To determine the relative volatility of any given two compounds, a method known as the PTx Method may be used. In this procedure, the total absolute pressure in a cell of known volume is measured at a constant temperature for various compositions of the two compounds. Use of the PTx Method is described in greater detail in "Phase Equilibrium in Process Design", Wiley-Interscience Publisher, 1970, written by Harold R. Null, on pages 124 to 126; hereby incorporated by reference.

These measurements can be converted into equilibrium vapor and liquid compositions in the PTx cell by using an activity coefficient equation model, such as the Non-Random, Two-Liquid (NRTL) equation, to represent liquid phase nonidealities. Use of an activity coefficient equation, such as the NRTL equation is described in greater detail in "The Properties of Gases and Liquids," $4^{th}$ edition, published McGraw Hill, written by Reid, Prausnitz and Poling, on pages 241 to 387, and in "Phase Equilibria in Chemical Engineering," published by Butterworth Publishers, 1985, written by Stanley M. Walas, pages 165 to 244. Both aforementioned references are hereby incorporated by reference.

Without wishing to be bound by any theory or explanation, it is believed that the NRTL equation, together with the PTx cell data, can sufficiently predict the relative volatilities of PFC-14, $NF_3$, and other compounds, and combinations and mixtures thereof, and can therefor predict the behaviour of PFC-14, $NF_3$ and other and mixtures in multi-stage separation equipment such as distillation columns.

By conventional distillation is meant that only the relative volatilities of the components of the mixture to be separated are used to separate the components.

By substantially free or substantially pure is meant that any given fluorinated compound other than the PFC-14 or $NF_3$ in the respective PFC-14 or $NF_3$ product is less than 10 parts-per-million-by-volume (ppm-volume) or 10 parts-per-million-molar (ppm-molar), more preferably less than 1 ppm-volume or 1 ppm-molar, most preferably less than 100 parts-per-billion-by-volume (ppbv) or 100 parts-per-billion-molar (ppb-molar). Alternately, by substantially free or substantially pure is meant that any given fluorinated compound other than the PFC-14 or $NF_3$ in the respective PFC-14 or $NF_3$ product is less than 10 parts-per-million-by-weight (ppm-weight), more preferably less than 1 ppm-weight, most preferably less than 100 parts-per-billion-by-weight (ppb-weight).

By high recovery efficiency is meant that greater than 90%, most typically greater than 95% of the PFC-14 or $NF_3$ in a first mixture is recovered as product substantially free of a specific fluorinated impurity.

By impurity is meant any fluorinated compound other than the PFC-14 or $NF_3$ that may be present in the respective PFC-14 or $NF_3$ product.

By azeotropic or azeotrope composition is meant a constant-boiling mixture of two or more substances that behaves as a single substance. One way to characterize an azeotropic composition is that the vapor produced by partial evaporation or distillation of the liquid has the same composition as the liquid from which it is evaporated or distilled, i.e., the mixture distills/refluxes without compositional change. Constant-boiling compositions are characterized as azeotropic because they exhibit either a maximum or minimum boiling point, as compared with that of the non-azeotropic mixture of the same components. Azeotropic compositions are also characterized by a minimum or a maximum in the vapor pressure measurements relative to the vapor pressure of the neat components in a PTx cell as a function of composition at a constant temperature.

By azeotrope-like is meant a composition that has a constant-boiling characteristic or a tendency not to fractionate upon boiling or evaporation. Therefore, the composition of the vapor formed is the same as or substantially the same as the original liquid composition. During boiling or evaporation, the liquid composition, if it changes at all, changes only to a minimal or negligible extent. An azeotrope-like composition can also be characterized by the area that is adjacent to the maximum or minimum vapor pressure in a plot of composition vapor pressure at a given temperature as a function of mole fraction of components in the composition. A composition is azeotrope-like if, after about 50 weight percent of an original composition is evaporated or boiled off to produce a remaining composition, the change between the original composition and the remaining composition is typically no more than about 6 weight % and typically no more than about 3 weight % or less relative to the original composition.

By high-boiling azeotrope is meant that an azeotropic or azeotrope-like composition boils at a higher temperature at any given pressure than any one of the compounds that comprise it would separately boil at that pressure. Alternately, by high-boiling azeotrope is meant any azeotropic or azeotrope-like composition that has a lower vapor pressure at any given temperature than any one of the compounds that comprise it would separately have at that temperature.

By low-boiling-azeotrope is meant that an azeotropic or azeotrope-like composition boils at a lower temperature at any given pressure than any one of the compounds that comprise it would separately boil at that pressure. Alternately, by low-boiling azeotrope is meant any azeotropic or azeotrope-like composition that has a higher vapor pressure at any given temperature than the vapor pressure of any one of the compounds that comprise the azeotrope would separately have at that temperature.

It is possible to characterize an azeotropic or azeotrope-like composition as a substantially constant-boiling admixture that may appear under many guises, depending upon the conditions chosen, by several criteria:

The composition can be defined as an azeotrope of two compounds because the term "azeotrope" is at once both definitive and limitative, and requires effective amounts of those two or more compounds for this unique composition of matter which can be a constant-boiling composition.

It is well known by those skilled in the art, that, at different pressures, the composition of a given azeotrope or azeotrope-like composition will vary at least to some degree, as will the boiling point temperature. Thus, an azeotropic or azeotrope-like composition of two compounds represents a unique type of relationship but with a variable composition which depends on temperature and/or pressure. Therefore, compositional ranges, rather than fixed compositions, are often used to define azeotropes and azeotrope-like compositions.

An azeotrope or azeotrope-like composition of two compounds can be characterized by defining compositions characterized by a boiling point at a given pressure, thus giving identifying characteristics without unduly limiting the scope of the invention by a specific numerical composition, which is limited by and is only accurate as the analytical equipment available.

It is recognized in the art that both the boiling point and the weight (or mole) percentages of each component of the azeotropic composition may change when the azeotrope or azeotrope-like liquid composition is allowed to boil at different pressures. Thus, an azeotropic or an azeotrope-like composition may be defined in terms of the unique relationship that exists among components or in terms of the exact weight (or mole) percentages of each component of the composition characterized by a fixed boiling point at a specific pressure.

By entraining agent is meant any compound that, when added to a first mixture, interacts with the components in that first mixture in a way that changes the relative volatilities of the components in the first mixture to each other such that those components may then be separated by distillation.

By azeotropic distillation is meant a process in which a distillation column is operated under conditions to cause an azeotropic or azeotrope-like composition to form, and the formation thereof changes the relative volatility of the components to each other such that the components may be separated by distillation. Azeotropic distillations may occur where only the components of the mixture to be separated are distilled, or where an entraining agent is added that forms an azeotrope with one or more of the components of the initial mixture. Entraining agents that act in this manner, that is to say, that form an azeotrope with one of more of the components of the mixture to be separated thus facilitating the separation of those components by distillation, are more commonly called azeotroping agents or azeotropic entraining agents.

By extractive distillation is meant a process in which an entraining agent is introduced at an upper feed point of the distillation column, whereas the mixture requiring separation is introduced at the same or preferably a relatively lower feed point of the column than the entraining agent. The entraining agent passes downwardly through trays or packing located in the column and exits the column bottoms with one or more components of the mixture to be separated. While in the presence of the entraining agent, at least one of the components to be separated becomes relatively more volatile compared to the other fluorinated compound(s) of the mixture, with that more volatile fluorinated component of the initial mixture exiting the column overheads. Entraining agents which are fed to a distillation column at a point equal to, or higher than, the mixture to be separated and which pass down through the column thus enabling a separation by distillation, are more commonly called extractive agents or extractants.

In conventional, azeotropic, or extractive distillations, the overhead or distillate stream exiting the column may be condensed using conventional reflux condensers. At least a portion of this condensed stream can be returned to the top of the column as reflux, and the remainder recovered as product or for optional processing. The ratio of the condensed material which is returned to the top of the column as reflux to the material removed as distillate is commonly referred to as the reflux ratio. The compounds and entraining agent exiting the column as distillate or distillation bottoms stream can then be passed to a stripper or second distillation column for separation by using conventional distillation, or may be separated by other methods. If desired, the entraining agent may then be recycled back to the first distillation column for reuse.

The specific conditions which can be used for practicing the invention depend upon a number of parameters, such as the diameter of the distillation column, feed points, number of separation stages in the column, among others. The operating pressure of the distillation system may range from about 15 to 500 psia, normally about 50 to 400 psia. Typically, an increase in the extractant or azeotroping agent feed rate relative to the feed rate of the mixture to be separated causes an increase in the purity of the product to be recovered with regard to those compound(s) being removed. Normally, increasing the reflux ratio results in increased distillate stream purity, but generally the reflux ratio ranges between 1/1 to 200/1. The temperature of the condenser, which is located adjacent to the top of the column, is normally sufficient to substantially fully condense the distillate that is exiting from the top of the column, or is that temperature required to achieve the desired reflux ratio by partial condensation.

The problems associated with conventional distillation can be solved by a distillation process using entraining agents. This method may be employed when the components of the mixture have relative volatilities that do not allow effective separation of the components by conventional distillation. In distillation using entraining agents, an entraining agent is added that causes the relative volatilities of the components in the starting mixture to be altered such that the relative volatility becomes sufficient to permit separation of the components. The difficulty in applying this method is that there is no known way, short of experimentation, of predicting which if any compound will be an effective entraining agent.

The first mixture can be obtained from any suitable manufacturing process or source which produces or generates a mixture comprising at least one of PFC-14 and $NF_3$. For example: PFC-14 may be produced by reacting a chlorocarbon or chlorofluorocarbon with HF; $NF_3$ may be produced by reacting ammonia ($NH_3$) with elemental fluorine ($F_2$). Alternately, the first mixture can be obtained from any suitable manufacturing process that uses any one of PFC-14 or $NF_3$ and desires to recover said PFC-14 or $NF_3$ from said process. Methods such as conventional distillation would then be used for removing inert carrier gases and for reducing initial amounts of other fluorinated impurities. The PFC-14 or $NF_3$ containing stream then may be processed in accordance with the inventive process for recovering and purifying PFC-14 or $NF_3$.

$NF_3$ and PFC-14, in their separated and pure states have normal boiling points of −129.1 and −128.1° C. These close boiling points alone would make efficient separation of $NF_3$ and PFC-14 extremely difficult by conventional distillation. However, mixtures of $NF_3$ and PFC-14 in addition form azeotropic or azeotrope-like compositions which makes their complete separation by conventional distillation impossible.

It is desirable to purify and recover separate product streams of each of PFC-14 and $NF_3$ that are substantially free of other fluorinated components. The present inventors have found that $NF_3$ and PFC-14 form an azeotropic or azeotrope-like compositions over a range of temperatures and pressures, and that $NF_3$ and PFC-14 can be partially purified by using said $NF_3$/PFC-14 azeotropic and azeotrope-like compositions. For example, a conventional distillation column can be operated at a pressure and temperature that causes an azeotropic or azeotrope-like composition to form. If the quantity of $NF_3$ versus PFC-14 in the column is greater than that in the azeotropic or azeotrope-like composition, a $NF_3$ product can be removed from the bottom of the column with the PFC-14 concentration in it reduced compared to the PFC-14 concentration in the $NF_3$/PFC-14 containing mixture initially fed or charged to the distillation column, while the azeotropic or azeotrope-like composition is removed from the top of the column. Conversely, if the quantity of PFC-14 versus $NF_3$ in the column is greater than that in the azeotropic or azeotrope-like composition, a PFC-14 product can be removed from the bottom of the column with the $NF_3$ concentration in it reduced compared to the $NF_3$ concentration in the $NF_3$/PFC-14 containing mixture initially fed or charged to the distillation column, while the azeotropic or azeotrope-like composition is removed from the top of the column. Obtaining a $NF_3$ product stream with the concentration of PFC-14 in it reduced compared to a first mixture with PFC-14 or obtaining a PFC-14 product stream with the concentration of $NF_3$ reduced compared to a first mixture with $NF_3$ in a single distillation would require starting with a composition higher in $NF_3$ or PFC-14 respectively than the azeotrope, but some portion of the $NF_3$ or PFC-14 respectively would necessarily remain as the $NF_3$/PFC-14 azeotrope.

The $NF_3$ can be partially separated from the PFC-14 by a series of multiple distillations performed at alternately higher and lower pressures that comprises forming these low-boiling, high-pressure azeotropes or azeotrope-like $NF_3$ and PFC-14 containing compositions within conventional distillation columns by taking advantage of changes in the $NF_3$/PFC-14 azeotrope composition that occur with pressure. By taking the overhead distillate from a column that is operated under conditions such that one component is in excess to the azeotrope (a first distillation), then feeding that distillate to a column operated under conditions such that the other component is in excess of the azeotrope (a second distillation), then feeding the distillate from the second distillation to a column where we repeat the sequence, that is, where the next column is again operated under conditions such that the first component is in excess, it is possible to produce a bottoms product of $NF_3$ from one distillation and of PFC-14 from a second distillation each of which has had the concentration of the other component reduced compared to a first mixture comprising $NF_3$ and PFC-14. This separation by "pressure-swing" distillation is possible only due to the unusual composition change of the azeotrope with pressure or temperature.

However, in these cases, where only the relative volatility of the $NF_3$/PFC-14 azeotrope compared to $NF_3$ or PFC-14 present in excess of the azeotrope is used as the basis for their separation, such separations would require tall and expensive distillation columns, and it would still be impossible to produce a substantially pure $NF_3$ or PFC-14 product from a $NF_3$/PFC-14 containing starting mixture.

The present inventors have found that PFC-14 may be separated from a variety of fluorinated compounds to produce a substantially pure $NF_3$ by the use of entraining agents in an azeotropic distillation process. For example, PFC-14 can be efficiently separated from $NF_3$ by the addition of HCl to a first mixture as an entraining agent, forming a second mixture, distilling the second mixture under conditions so as to form a azeotropic or azeotrope-like composition comprising HCl and PFC-14, and distilling the PFC-14 and HCl azeotropic composition overhead from the column. The PFC-14 in the distillate may then optionally be separated from the HCl, for example by water washing or by use of a semi-permeable membrane which preferentially allows HCl to pass through versus the PFC-14 or by other commonly known techniques, and the PFC-14 recovered as substantially pure product.

HCl forms azeotropic or azeotrope-like compositions with a number of the fluorinated compounds typically found in the exhaust gas obtained from integrated manufacturing processes. Examples of azeotropic or azeotrope-like compositions that may be formed between HCl and these fluorinated compounds are shown in Table 1. In Table 1, mixtures comprising compound "A" and compound "B" form low-boiling azeotropic or azeotropic-like compositions comprising the specified moles of compound "A" and the specified moles of compound "B" and having the specified pressure at the indicated temperature

TABLE 1

| Compound "A" | Moles "A" | Compound "B" | Moles "B" | Temp ° C. | Pressure psia |
|---|---|---|---|---|---|
| HCl | 9.6  | PFC-14    | 90.4 | −65 | 311 |
| HCl | 6.8  | $NF_3$    | 93.2 | −78 | 196 |
| HCl | 63.5 | PFC-116   | 36.5 | −20 | 321 |
| HCl | 89.4 | PFC-218   | 10.6 | −20 | 226 |
| HCl | 3.2  | $CO_2$    | 96.8 | −15 | 332 |
| HCl | 70.4 | $SF_6$    | 29.6 | −15 | 321 |
| HCl | 17.3 | $N_2O$    | 82.7 | −20 | 263 |
| HCl | 52.6 | Ethane    | 47.4 | −25 | 244 |
| HCl | 68.3 | $CF_2=CF_2$ | 31.7 | −20 | 261 |

The present inventors have found that HCl and PFC-14 form azeotropic or azeotrope-like compositions over a range of temperatures and pressure. Surprisingly, the HCl/PFC-14 azeotropic or azeotrope-like compositions have the lowest boiling point temperature at any given pressure, and the highest vapor pressure at any given temperature of either the pure components or the azeotropic compositions comprising HCl and the pure components shown in Table 1. By distilling mixtures comprising PFC-14 in the presence of HCl, and distilling under conditions so as to form the PFC-14/HCl azeotrope, the HCl/PFC-14 azeotropic or azeotrope-like composition may be recovered as overhead distillate that is substantially free of the other compounds while the other compounds are recovered from the column bottoms. HCl may optionally then be separated from the PFC-14, for example, by water washing or by use of a semi-permeable membrane or other commonly known techniques and the PFC-14 recovered.

Certain aspects of the present invention can be better understood by reference to FIG. 1. FIG. 1 schematically illustrates a system that can be used for performing one aspect of the inventive distillation process. A first mixture comprising $NF_3$ and PFC-14 is supplied via conduit 1 to distillation column 2. At least one azeotropic agent, e.g., HCl, is supplied via conduit 3 to distillation column 2. The entraining agent may alternately be mixed with the $NF_3$ and PFC-14-containing mixture prior to the distillation column and simultaneously fed in via conduit 1. The column is operated under conditions such that a lower-boiling azeotropic or azeotrope-like mixture is formed between the PFC-14 and azeotropic agent. $NF_3$ substantially free of PFC-14 is recovered out the distillation column bottoms via conduit 4. The distillate from the column comprising PFC-14 and the azeotropic agent exits via conduit 5 and is fed to the column condenser 6. Part of the condensed distillate is returned to the distillation column as reflux via conduit 7. The remainder of the condensed distillate comprising PFC-14 and the azeotropic agent may be recovered, or optionally separated to separately recover the PFC-14 and azeotropic agent.

For example, where HCl is used as the azeotropic agent for this process, the HCl may be removed from the PFC-14 distillate product by water washing then drying the PFC-14 stream, thus recovering PFC-14 substantially free of either $NF_3$ or HCl. Alternately, where HCl is used as the azeotroping agent for this process, a stream comprising an azeotropic or azeotrope-like composition comprising HCl and PFC-14 may be sent via conduit 8 to cooler 9 then to a suitable separation unit 10, e.g., a membrane separation unit, where the HCl-containing mixture is separated into two streams, one higher in concentration in HCl (HCl-enriched) 11 and the other lower in HCl concentration (HCl-depleted) 12 compared to the column 2 distillate mixture. The HCl-enriched stream 11 may be recycled back via conduit 13 to be mixed with the feed to distillation column 2. The HCl-depleted stream 12 may be sent to distillation column 14 via conduit 15 where column 14 is operated under conditions to form an azeotrope comprising HCl and PFC-14. Because the HCl and PFC-14 containing stream fed to this second distillation is higher in PFC-14 concentration versus the HCl and PFC-14 azeotrope, by operating the column under conditions such that an azeotropic or azeotrope-like mixture of HCl and PFC-14 is formed, PFC-14 substantially free of HCl will exit the column bottoms via conduit 16. The column distillate comprising HCl and PFC-14 exit overhead column 14 and is fed via conduit 17 to condenser 18. At least part of the liquid condensate is returned via conduit 19 to the column as reflux, while the remainder is recycled via conduit 20 to mix with the streams being fed to separator 10.

In FIG. 1, the HCl-enriched stream 11 may be alternately sent to distillation column 21 via conduit 22, where column 21 is operated under conditions to form an azeotrope comprising HCl and PFC-14. Because the HCl and PFC-14-containing stream fed to this second distillation is higher in HCl concentration versus the HCl and PFC-14 azeotropic or azeotrope-like composition, by operating the column under conditions such that an azeotropic or azeotrope-like mixture of HCl and PFC-14 is formed, HCl substantially free of PFC-14 will exit the column bottoms via conduit 23. The column distillate comprising HCl and PFC-14 exit overhead column 21 and is fed via conduit 24 to condenser 25. At least part of the liquid condensate is returned via conduit 26 to the column as reflux, while the remainder is recycled via conduit 27 to mix with the feed steams to separator 10.

In another aspect of the current invention, we have found that $NF_3$ and PFC-14 may be separated from each other and other fluorinated impurities by the use of entraining agents in an extractive distillation process. Suitable entraining agents that may be used as extractants for the separation of $NF_3$ and PFC-14 include: hydrocarbons, hydrofluorocarbons, hydrochlorofluorocarbons, hydrochlorocarbons, hydrogen chloride and both organic and inorganic oxides. Entraining agents have normal boiling points of from about −110° C. to about −25° C. Hydrocarbons include ethane, ethylene, propane, and propylene. Hydrofluorocarbons include methyl fluoride (HFC-41), difluoromethane (HFC-32), 1,1,1-trifluoroethane (HFC-143a), pentafluoroethane (HFC-125), and fluoroethane (HFC-161). Hydrochlorofluorocarbons include chlorodifluoromethane (HCFC-22). Hydrochlorocarbons include methyl chloride (HCC-40). Oxides include nitrous oxide ($N_2O$), carbon dioxide ($CO_2$), carbonyl fluoride ($COF_2$), and perfluoroacetyl fluoride ($CF_3COF$).

The preferred single component entraining agents for separating PFC-14 and $NF_3$ by extractive distillation include nitrous oxide ($N_2O$), chlorodifluoromethane (HCFC-22), difluoromethane (HFC-32), fluoroethane (HFC-161) and methyl fluoride (HFC-41). Most preferred are nitrous oxide and HCFC-22 as extractants for the separation. Although HFC-32, HFC-161 and HFC-41 each require fewer theoretical distillation column stages, lower extractant flow rates, or both, than either nitrous oxide or HCFC-22 to effect an equivalent reduction of PFC-14 in a $NF_3$ product stream, it was found that nitrous oxide and HCFC-22 are less likely to react in a mixture with $NF_3$ than HFC-32, HFC-161 and HFC-41.

These single component entraining agents may be used alone or in combination with each other as the extractants for this separation. For example, $N_2O$ forms an azeotropic or azeotrope-like composition with each of HFC-23 and HCl. The respective $N_2O$/HFC-23 and $N_2O$/HCl azeotropic or azeotrope-like compositions may each be employed as the extractant for separating $NF_3$ and PFC-14.

Figure 2:
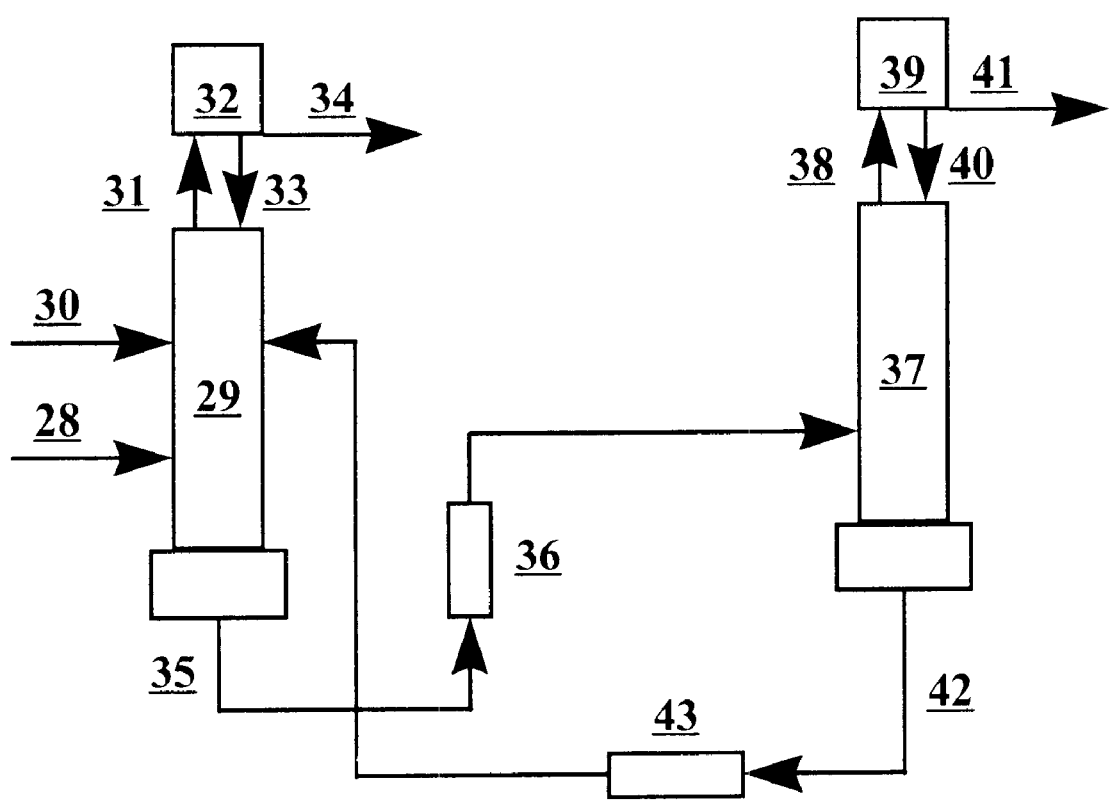
FIG. 2 is a schematic diagram of a distillation system that can be used for practicing an aspect of the present process

FIG. 2 schematically illustrates a system that can be used to perform aspects of the inventive extractive distillation process. A first mixture comprising PFC-14 and $NF_3$ is supplied via conduit 28 to distillation column 29. At least one extractive agent, e.g., ethane, is supplied via conduit 30 to distillation column 29 at a feed point higher in the column than the feed point of the mixture to be separated, e.g., PFC-14 and $NF_3$. The overhead distillate from the column is sent via conduit 31 to condenser 32. At least part of the condensed distillate stream is returned to the column 29 as reflux via conduit 33. The remainder of the condensed distillate is recovered via conduit 34 as PFC-14 product substantially free of $NF_3$ and ethane. A stream comprising ethane and $NF_3$ substantially free of PFC-14 is removed from the column 29 bottoms via conduit 35 and may be recovered as product. Alternately, the column bottoms stream 35 may be sent to optional cooler 36 and from there fed to distillation column 37, which is operated so as to strip compounds other than the entraining agent from the entraining agent. The distillate from column 37 may be fed via conduit 38 to condenser 39. From condenser 39 some amount of condensed distillate may be returned to the column 37 as reflux via conduit 40 while the remainder recovered as product, e.g., as $NF_3$ substantially free of PFC-14 and extractive agent, via conduit 41. Extractive agent, e.g., ethane, with the concentration of non-ethane compounds reduced compared to their concentrations in stream 35 is obtained as the distillation column bottoms 42. Stream 42 may optionally be fed to cooler 43 and then returned to distillation column 29 as extractant feed, fed to the column at a feed point higher in the column than that feed point of the mixture to be separated, e.g., PFC-14 and $NF_3$, or may be optionally mixed with stream 30.

EXAMPLES

The following Examples are provided to illustrate certain aspects of the present invention, and are not intended to limit the scope of the invention. The following Examples employ the NRTL equations identified above. In the following Examples, each stage is based upon a 100% operational or performance efficiency. The total stages include condenser and reboiler, with the condenser counted as stage No. 1. In the following Examples, flow rates are given in pounds (weight)-per-hour (pph) or pound-moles-per-hour (mph); temperatures are expressed in degrees Celsius (° C.); pressures are expressed in pound-per-square-inch-absolute (psia); stream concentrations are expressed in parts-per-million-by-weight (ppmw or ppm-weight) or parts-per-million-by-moles (ppmm or ppm-molar); heat flow rates removed by the condenser or put into the reboiler of the distillation columns are expressed in pcu/hour or pcu/hr.

Comparative Example 1

In this Comparative Example, a crude feed stream comprising $NF_3$ and PFC-14 is fed to a distillation column operated under the five sets of conditions (cases) shown in Table 2, with the results of the distillations shown in the respective columns. The distillation columns in these Cases are operated to remove a PFC-14 product from the column as overhead distillate and a $NF_3$ product as column bottoms.

In Case 1 of this Comparative Example, a crude 100 pph $NF_3$ feed stream containing 10,000 ppm-weight of PFC-14 is feed to a distillation column. The column has 200 stages. The reflux ratio is approximately 5000:1. As may be seen in this Case, even when 20% of the $NF_3$ feed to the column is taken overhead, the concentration of PFC-14 in the $NF_3$ bottoms product is only reduced to 211 ppm-weight.

Compared to Case 1, in Case 2 of this Comparative Example the PFC-14 concentration in the crude $NF_3$ stream fed to the column has been reduced to 1,000 ppm-weight, the reflux rate has been increased to 500,000 pph, the distillate takeoff rate has been decreased to 0.5 pph, and the bottoms takeoff rate has been increased to 99.5. As may be seen in this Case, the PFC-14 concentration in the $NF_3$ bottoms product is still only reduced to 484 ppm-weight.

Compared to Case 2, in Case 3 of this Comparative Example the overhead distillate rate is increased to 5.0 pph and the bottoms takeoff rate has been decreased to 95.0 pph. As may be seen in this Case, the $NF_3$ bottoms takeoff product still contains 65 ppm-weight PFC-14, even though 5% of the $NF_3$ feed is being lost in the overhead distillate.

In Case 4 of this Comparative Example, the feed to the distillate column is a 60/40 molar ratio of $NF_3$/PFC-14, which comprises approximately the azeotropic or azeotrope-like composition formed by $NF_3$ and PFC-14 at −75° C. In spite of allowing more than 50% of the $NF_3$ fed to be removed overhead in the distillate, there is essentially no change in either the distillate or bottoms product compositions compared to the composition of the crude feed stream.

In Case 5 of this Comparative Example, the number of column stages in Case 4 is doubled, and the reflux rate increased. In spite of this, there is still essentially no substantial change in either the distillate or bottoms product composition compared to the composition of the crude feed stream.

The Cases in this Comparative Examples show that, even with many distillation column stages and extremely high reflux ratios, it is impossible to recover a $NF_3$ product by conventional distillation from a first mixture comprising $NF_3$ and PFC-14 where said $NF_3$ is recovered substantially free of PFC-14 and with high recovery efficiency. The $NF_3$ product purity and recovery efficiency in such distillations is limited because an azeotropic or azeotrope-like composition is formed between $NF_3$ and PFC-14.

However, Cases 1, 2 and 3 of this Comparative Example do show that by operating a distillation column under conditions such that azeotropic or azeotrope-like compositions of $NF_3$ and PFC-14 are formed and where said $NF_3$/PFC-14 azeotropic or azeotrope-like compositions are higher in PFC-14 concentration than the $NF_3$/PFC-14 concentration in a first mixture, PFC-14 may be removed from the $NF_3$ of a first mixture. By distilling the $NF_3$/PFC-14 azeotropic or azeotrope-like composition formed as overhead distillate, an $NF_3$ product may be recovered as distillation column bottoms where the concentration of the PFC-14 in said $NF_3$ product has been reduced compared to the first mixture. However, since some portion of the $NF_3$ in the first mixture necessarily remains with the PFC-14 removed in the distillate, only a limited recovery efficiency of the $NF_3$ fed in the first mixture is possible.

Example 1

In each Case of this Example, a crude $NF_3$ feed stream comprising $NF_3$ and PFC-14 is fed to a distillation column. HCl is also added to the distillation column. The distillation column is operated to recover a PFC-14 product from the column as overhead distillate, while a $NF_3$ product is recovered as column bottoms. The conditions and the results of the distillations for each Case are shown in Table 3.

In Case 1, the crude $NF_3$ feed stream comprises $NF_3$ containing 1000 ppm-weight of PFC-14 and the crude stream feed rate is 100 pph. 1 pph of HCl is fed to the column as an entraining agent. The column has 122 stages and the reflux ratio is 5000:1. The distillate rate is 10 pph, such that approximately 10% of the $NF_3$ in the crude feed stream exits overhead with the PFC-14 distillate product. As a result of this distillation, a $NF_3$ bottoms product is obtained that contains 85 ppm-weight PFC-14.

In Case 2, the number of column stages is increased to 244. As a result of this distillation, a $NF_3$ bottoms product is obtained that contains 1.2 ppm-weight PFC-14.

In Case 3, the crude $NF_3$ feed stream instead contains 100 ppm-weight PFC-14 and the reflux rate is 22,000 pph. As a result of this distillation, a $NF_3$ bottoms product is obtained that contains about 10 ppm-weight PFC-14.

In Case 4, the distillate takeoff rate is changed to 20 pph. As a result of this distillation, a $NF_3$ bottoms product is obtained that contains about 5 ppm-weight PFC-14.

The Cases of this Example show that by adding or having present HCl in a mixture comprising $NF_3$ and PFC-14, then by distilling the mixture under conditions sufficient to form the PFC-14/HCl azeotrope, the PFC-14 may be separated from the $NF_3$. The PFC-14 is recovered in the distillate as the HCl/PFC-14 azeotrope, and a $NF_3$ product may be recovered as columns bottoms substantially free of PFC-14 and with high recovery efficiency of the $NF_3$.

Example 2

In each Case of this Example, a crude NF$_3$ feed stream comprising NF$_3$ and PFC-14 is fed to a distillation column operated under the conditions shown in Table 4. The concentration of the PFC-14 in the feed stream is 10,000 ppm-molar. A different compound is fed to the column as an extractive agent in each Case. The columns in these Cases are operated to remove PFC-14 from the column as overhead distillate, while recovering a NF$_3$ product as column bottoms. The results of the distillations are shown in Table 4. In this Example, the concentration of PFC-14 and NF$_3$ shown in each of the column bottoms streams is calculated versus the total weight or moles of PFC-14 and NF$_3$ in that stream only, and ignore the weight or moles of any extractant present.

In Table 4, PFC-218 is perfluoropropane or octafluoropropane (C$_3$F$_8$); PFC-116 is perfluoroethane or hexafluoroethane (C$_2$F$_6$), CFC-13 is chlorotrifluoromethane (CClF$_3$), CFC-115 is chloropentafluoroethane (C$_2$ClF$_5$), HFC-125 is pentafluoroethane (C$_2$HF$_5$), CO$_2$ is carbon dioxide, HFC-143a is trifluoroethane (C$_2$H$_3$F$_3$), HFC-23 is trifluoromethane (CHF$_3$), N$_2$O is nitrous oxide, C$_2$H$_6$ is ethane, HFC-41 is fluoromethane (CH$_3$F), HCl is hydrogen chloride, HCC-40 is chloromethane (CH$_3$Cl), HCFC-22 is chlorodifluoromethane (CHClF$_2$), HFC-32 is difluoromethane (CH$_2$F$_2$), HFC-161 is fluoroethane (C$_2$H$_5$F).

In Cases 1 and 2, where PFC-218 and PFC-116 are respectively fed as the extractive agent, the concentration of PFC-14 in the NF$_3$ column bottoms product is essentially unchanged from that of the crude feed stream. For example, Cases 1 and 2 show a PFC-14 concentration of 10,000 ppm-molar in the crude feed stream, while the PFC-14 concentration in the column bottoms is 10,100 ppm-molar with PFC-116 as the extractive agent and 9,110 ppm-molar with PFC-218 as the extractive agent. Cases 1 and 2 are comparative Cases that show fully-fluorinated compounds such as PFC-218 and PFC-116 are ineffective as extractive agents for separating PFC-14 from NF$_3$.

By contrast, Cases 3 through 16 show their respective extractive agents are effective for separating PFC-14 from NF$_3$, such that NF$_3$ having significantly reduced concentrations of PFC-14 versus the crude feed stream may be recovered as a NF$_3$ product from the distillation column bottoms.

The effectiveness of the extractive agents generally increase from Cases 3 through 16, as indicated by the fact that lower residual PFC-14 concentrations in the NF$_3$ product bottoms stream are obtained in Cases 3 through 8, and lower extractive agent flow rates on a molar basis are required for Cases 9 through 16 to achieve the same residual PFC-14 concentration in the NF$_3$ bottoms product. Thus, N$_2$O, C$_2$H$_6$, HFC-41, HCl, HCC-40, HCFC-22, HFC-32 and HFC-161 from Cases 9 through 16, respectively, are more effective than CO$_2$, HFC-143a and HFC-23 from Cases 6 through 8, respectively, which are in turn more effective than CFC-13, CFC-115 and HFC-125 from Cases 3 through 5, respectively. The extractive agents of Cases 9 through 16 are particularly effective in the separation, producing an NF$_3$ product containing about 0.1 ppm-molar PFC-14 or less than about 0.13 ppm-weight PFC-14, and in recovering said NF$_3$ product with greater than 99% recovery efficiency from the crude feed stream.

The extractive agent indicated may optionally be separated from the extractive distillation column bottoms by distillation or other methods disclosed in the present specification, and an NF$_3$ product that is substantially free of both PFC-14 and extractive agent may be recovered.

Example 3

In the Cases of this Example, a crude feed stream comprising 99.19 pph PFC-14 and 0.81 pph NF$_3$ is fed to a distillation column. A different entraining agent is fed as an extractant to the columns in each Case. The columns in these Cases are operated to recover a PFC-14 product from the column as overhead distillate, while removing NF$_3$ in the column bottoms. The extractive agents used and the results of these distillations are shown in Table 5.

The Cases from this Example show that the extractive agents of the current invention are also effective for removing NF$_3$ from a stream comprising PFC-14 and NF$_3$, such that a PFC-14 product substantially free of NF$_3$ may be recovered with high recovery efficiency.

Example 4

In the four Cases of this Example, a crude feed stream comprising 45 pph NF$_3$ and 55 pph PFC-14 is fed to distillation columns having the same number of stages, operated at the same pressure, with extractive agent flow rate and feed points in the column chosen to give the desired separation. In all Cases the distillation is operated so that a NF$_3$ product is recovered as distillation column bottoms with a PFC-14 product removed as overhead distillate. N$_2$O is fed as the extractive agent in Cases 1 and 3, and HCFC-22 is fed as the extractive agent in Cases 2 and 4. The results of these distillations are shown in Table 6.

As may be seen, Cases 1 and 2 recover a NF$_3$ bottoms product stream in which the PFC-14 concentration is 0.1 ppm-molar versus the NF$_3$ in that stream, with the NF$_3$ recovery being about 96% of the NF$_3$ originally fed. Cases 3 and 4 recover a PFC-14 overhead distillate product stream in which the NF$_3$ concentration is 0.1 ppm-molar versus the PFC-14 in that stream, with that PFC-14 recovery being about 98% of the PFC-14 originally fed.

This Example shows the versatility of the instant extractive distillation invention, where the same distillation column can be employed to produce either PFC-14 substantially free of NF$_3$ or produce NF$_3$ substantially free of PFC-14, each with high recovery efficiency, from the same feed stream, and even when said feed stream contains high concentrations of the component that needs to be removed. Changing the operation of the column to alternate between recovering higher purity NF$_3$ or higher purity PFC-14 as product is effected simply by changing the crude feed and extractive agent feed points on the column, raising the feed and extractive agent feed points for high purity NF$_3$ product recovery, lowering the feed and extractive agent feed points for high-purity PFC-14 product recovery, and by adjusting the reflux rate, extractive agent feed rate, and crude fed rate as necessary to achieve 99.9999% or greater product purity.

Example 5

In the Cases of this Example, a crude feed stream comprising 98.76 pph NF$_3$ and 1.24 pph PFC-14 is fed to one or more distillation columns. The conditions and results of the distillations are shown in Table 7 (conventional distillation) and in Table 8 (extractive distillation).

Case 5 shown in Table 8 illustrates the complete extractive distillation process, including extraction column, stripping column and extractive agent feed cooler as shown in FIG. 2. N$_2$O is used as the extractive agent. Case 5 is similar to Case 9, Table 4, which also used N$_2$O as the extractive agent. In this Example, Case 5, the stripping column tails stream, which contains small amounts of PFC-14 and NF$_3$ is recycled back to the top of the extraction column. As can be seen in Table 8, the extraction column bottoms stream contains 0.1 ppm-molar PFC-14 versus $NF_3$, just as it did in Case 9, Table 4. The extraction column bottoms stream is fed to the stripping column where the $NF_3$ product is removed overhead in the distillate stream, still containing 0.1 ppm-molar PFC-14 and non-detectable amounts of the extractive agent $N_2O$. This Example illustrates the operation of the stripping column and it demonstrates it is possible to produce $NF_3$ product which is substantially free of all other impurities ($NF_3$ purity 99.9999% or higher).

Case 1 in Table 7 uses a single distillation column with 195 stages, which is the same as the total number of stages for the combined extraction and stripping columns in Case 5, Table 8. No entraining agents are added. Case 1 in Table 7 has a total condenser refrigeration duty of −97500 pcu/hour, which is the same as the total combined refrigeration cooling duty for the extraction and stripping column condensers plus the recycle extractant cooler in Case 5, Table 8. In Case 1, the column is operated to remove PFC-14 in the overhead distillate and the $NF_3$ product as the column bottoms. The distillation produces a $NF_3$ product containing slightly reduced PFC-14 concentration, 7298 ppm-molar, versus the PFC-14 concentration in the crude column feed stream, 10000 ppm-molar. In Case 2, the conditions are similar to Case 1, but the distillate takeoff rate is increased ten times. The $NF_3$ bottoms product in Case 2, however, only decreases slightly in PFC-14 concentration compared to Case 1, from 7298 ppm-molar to 1969 ppm-molar. In Case 3, the conditions are similar to Case 1, but the reflux condenser duty is increased ten times. The PFC concentration in the $NF_3$ bottoms product in Case 3 again decreases only slightly compared to that of Case 1, from 7298 ppm-molar to 6253 ppm-molar. In Case 4, both the reflux condenser duty and the distillate rate are each increased ten times compared to Case 1. However, the $NF_3$ bottoms product still contains 287 ppm-molar PFC-14.

Cases 1 through 4 of this Example are comparative examples showing conventional distillation is ineffective in producing a $NF_3$ product stream that is substantially free of PFC-14. Case 5, which uses extractive distillation, clearly shows the significant improvement provided by the current invention in producing high-purity $NF_3$ product versus conventional techniques.

Example 6

In this Example, a crude feed stream comprising 98.76 pph $NF_3$ and 1.24 pph PFC-14 is fed to two distillation columns in an extractive distillation process which uses HCl as the extractive agent. The conditions and results of the distillations are shown in Case 1, Table 9. This Case is similar to Case 12, Table 4, which also used HCl as the extractive agent. This Case illustrates the complete extractive distillation process, including extraction column, stripping column and extractant feed cooler as shown in FIG. 2, and it also illustrates the use of the HCl/$NF_3$ azeotrope in a $NF_3$ purification process.

In the Example, the extraction column is operated under the same conditions as in Case 12, Table 4. The extraction column bottoms stream is fed to a stripping column operated under conditions to form an HCl/$NF_3$ azeotropic or azeotrope-like composition. Forming the the azeotropic or azeotrope-like composition allows $NF_3$ to be removed from the stripping column as overhead distillate such that an HCl product is recovered from the stripping column bottoms where said HCl product has a $NF_3$ concentration which is substantially reduced compared to the column feed stream. With this reduction in $NF_3$ concentration, this HCl product stream may then be recycled as extractive agent to the extraction column. Further, this reduces the volume of HCl that would otherwise be lost if it were removed by other conventional methods, such as if the HCl were removed from the $NF_3$ by water washing as might have been done with the extraction column bottoms stream of Case 12, Table 4.

By comparing this Example with Case 5 in Table 8, in which $N_2O$ is used as the extractive agent instead of HCl, it can be seen the use of HCl results in equivalent $NF_3$ product purity (>99.9999%) with fewer total column stages (152 versus 195) and with lower total refrigeration duty for the extraction and stripping columns and recycle cooler (−41200 pcu/hr versus −97500 pcu/hr). This further illustrates the effectiveness of the HCl/$NF_3$ azeotrope in the purification of $NF_3$.

Example 7

This Example demonstrates the existence of azeotropic or azeotrope-like compositions between the binary pairs mixtures consisting essentially of PFC-14 and $NF_3$; PFC-14 and HCl; $NF_3$ and HCl; $N_2O$ and HFC-23; and HCl and $N_2O$.

To determine the relative volatility of each binary pair, the PTx Method was used. In this procedure, for each binary pair, the total absolute pressure in a PTx cell of known volume was measured at constant temperature for various known binary compositions. These measurements were then reduced to equilibrium vapor and liquid compositions using the NRTL equation.

The vapor pressure measured versus the composition in the PTx cell for these binary systems are shown in FIGS. 3 through 7, respectively. The experimental data points are shown in each Figure as solid points and the solid line is drawn from data calculated using the NRTL equation.

Referring now to FIG. 3, FIG. 3 illustrates graphically the formation of an azeotropic and azeotrope-like composition consisting essentially of PFC-14 and $NF_3$ at −70.1° C., as indicated by a mixture of about 36 mole % PFC-14 and 64 mole % $NF_3$ having the highest pressure over the range of compositions at this temperature. Based upon these findings, it has been calculated that an azeotropic or azeotrope-like compositions of about 20 mole % PFC-14 and 80 mole % $NF_3$ is formed at −110° C. and 47 psia, and an azeotropic or azeotrope-like composition of about 55 mole % PFC-14 and 45 mole % $NF_3$ is formed at −40° C. and 645 psia. Accordingly, the present invention provides an azeotropic or azeotrope-like composition consisting essentially of from about 20 to about 55 mole % PFC-14 and from about 80 to about 45 mole % $NF_3$, said composition having a boiling point of from about −110° C. at 47 psia to about −40° C. at 645 psia.

Referring now to FIG. 4, FIG. 4 illustrates graphically the formation of an azeotropic and azeotrope-like composition consisting essentially of PFC-14 and HCl at −76° C. as indicated by a mixture of 91 mole % PFC-14 and 9 mole % HCl having the highest pressure over the range of compositions at this temperature. Based upon these findings, it has been calculated that an azeotropic or azeotrope-like compositions of about 93 mole % PFC-14 and 7 mole % HCl is formed at −100° C. and 77 psia and an azeotropic or azeotrope-like composition of about 91 mole % PFC-14 and 9 mole % HCl is formed at −50° C. and 497 psia. Accordingly, the present invention provides an azeotropic or azeotrope-like composition consisting essentially of from about 93 to about 91 mole % PFC-14 and from about 7 to about 9 mole % HCl, said composition having a boiling point of from about −100° C. at 77 psia to about −50° C. at 497 psia.

Referring now to FIG. 5, FIG. 5 illustrates graphically the formation of an azeotropic and azeotrope-like composition consisting essentially of $NF_3$ and HCl at −78° C., as indicated by a mixture of about 93 mole % $NF_3$ and 7 mole % HCl having the highest pressure over the range of compositions at this temperature. Based upon these findings, it has been calculated that an azeotropic or azeotrope-like compositions of about 94 mole % $NF_3$ and 6 mole % HCl is formed at −100° C. and 79 psia and an azeotropic or azeotrope-like composition of about 93 mole % $NF_3$ and 7 mole % HCl is formed at −50° C. and 487 psia. Accordingly, the present invention provides an azeotropic or azeotrope-like composition consisting essentially of from about 94 to about 93 mole % $NF_3$ and from about 6 to about 7 mole % HCl, said composition having a boiling point of from about −100° C. at 79 psia to about −50° C. at 487 psia.

Referring now to FIG. 6, FIG. 6 illustrates graphically the formation of an azeotropic and azeotrope-like composition consisting essentially of $N_2O$ and HFC-23 at −70° C., as indicated by a mixture of about 94 mole % $N_2O$ and 6 mole % HFC-23 having the highest pressure over the range of compositions at this temperature. Based upon these findings, it has been calculated that an azeotropic or azeotrope-like compositions of about 95 mole % $N_2O$ and 5 mole % HFC-23 is formed at −90° C. and 13 psia and an azeotropic or azeotrope-like composition of about 90 mole % $N_2O$ and 10 mole % HFC-23 is formed at 25° C. and 824 psia. Accordingly, the present invention provides an azeotropic or azeotrope-like composition consisting essentially of from about 95 to about 90 mole % $N_2O$ and from about 5 to about 10 mole % HFC-23, said composition having a boiling point of from about −90° C. at 13 psia to about 25° C. at 824 psia.

Referring now to FIG. 7, FIG. 7 illustrates graphically the formation of an azeotropic and azeotrope-like composition consisting essentially of $N_2O$ and HCl at −30.3° C., as indicated by a mixture of about 82 mole % $N_2O$ and 18 mole % HCl having the highest pressure over the range of compositions at this temperature. Based upon these findings, it has been calculated that an azeotropic or azeotrope-like compositions of about 76 mole % $N_2O$ and 24 mole % HCl is formed at −90° C. and 14 psia and an azeotropic or azeotrope-like composition of about 83 mole % $N_2O$ and 17 mole % HCl is formed at 25° C. and 828 psia. Accordingly, the present invention provides an azeotropic or azeotrope-like composition consisting essentially of from about 76 to about 83 mole % $N_2O$ and from about 24 to about 17 mole % HCl, said composition having a boiling point of from about −90° C. at 14 psia to about 25° C. at 828 psia.

TABLE 2

| | Case Number | | | | |
|---|---|---|---|---|---|
| | 1 | 2 | 3 | 4 | 5 |
| # of stages | 200 | 200 | 200 | 122 | 244 |
| Crude Feed Stage | 100 | 100 | 100 | 61 | 122 |
| Top Temperature (° C.) | −75 | −75 | −75 | −75 | −75 |
| Reflux Temperature (° C.) | −75 | −75 | −75 | −75 | −75 |
| Distillate Temperature (° C.) | −75 | −75 | −75 | −75 | −75 |
| Bottoms Temperature (° C.) | −74 | −74 | −74 | −75 | −75 |
| Crude Feed Temperature (° C.) | −75 | −75 | −75 | −75 | −75 |
| Top Pressure (psia) | 215 | 215 | 215 | 215 | 215 |
| Condenser Pressure (psia) | 215 | 215 | 215 | 215 | 215 |
| Bottoms Pressure (psia) | 220 | 220 | 220 | 220 | 220 |
| Crude Feed Rate (pph) | 100 | 100 | 100 | 100 | 100 |
| Distillate Takeoff Rate (pph) | 20 | 0.5 | 5 | 50 | 50 |
| Bottoms Takeoff Rate (pph) | 80 | 99.5 | 95 | 50 | 50 |
| Reflux Rate (pph) | 100000 | 500000 | 500000 | 3500 | 14000 |
| Distillate PFC-14 (pph) | 0.98 | 0.05 | 0.09 | 21.75 | 21.33 |
| $NF_3$ Loss Overhead (pph) | 19.02 | 0.45 | 4.91 | 28.25 | 28.67 |
| $NF_3$ in Feed That Is Lost Overhead (%) | 19.2 | 0.45 | 4.9 | 51.6 | 52.4 |
| Feed to Column | | | | | |
| $NF_3$ (ppmw) | 990000 | 999000 | 999000 | 547552 | 547552 |
| PFC-14 (ppmw) | 10000 | 1000 | 1000 | 452448 | 452448 |
| $NF_3$ (ppmm) | 991916 | 999193 | 999193 | 600000 | 600000 |
| PFC-14 (ppmm) | 8084 | 807 | 807 | 400000 | 400000 |
| Distillate from Column | | | | | |
| $NF_3$ (ppmw) | 950843 | 896360 | 981229 | 564949 | 573322 |
| PFC-14 (ppmw) | 49157 | 103640 | 18771 | 435051 | 426678 |
| $NF_3$ (ppmm) | 959960 | 914675 | 984800 | 616792 | 624830 |
| PFC-14 (ppmm) | 40040 | 85325 | 15200 | 383208 | 375170 |
| Bottoms from Column | | | | | |
| $NF_3$ (ppmw) | 999789 | 999516 | 999935 | 530155 | 521781 |
| PFC-14 (ppmw) | 211 | 484 | 65 | 469845 | 478219 |
| $NF_3$ (ppmm) | 999830 | 999609 | 999948 | 583084 | 574897 |
| PFC-14 (ppmm) | 170 | 391 | 52 | 416916 | 425103 |
| $NF_3$ Recovery Efficiency (%) | 81 | 99.5 | 95 | 48.4 | 47.6 |

TABLE 3

| | Case Number | | | |
|---|---|---|---|---|
| | 1 | 2 | 3 | 4 |
| # of Stages | 122 | 244 | 122 | 122 |
| Crude Feed Stage | 60 | 122 | 60 | 60 |
| HCl Feed Stage | 20 | 20 | 20 | 20 |
| Top Temperature (° C.) | −92 | −92 | −92 | −92 |
| Reflux Temperature (° C.) | −92 | −92 | −92 | −92 |
| Distillate Temperature (° C.) | −92 | −92 | −92 | −92 |
| Bottoms Temperature (° C.) | −90 | −90 | −90 | −90 |
| Crude Feed Temperature (° C.) | −91 | −91 | −91 | −91 |
| Top Pressure (psia) | 115 | 115 | 115 | 115 |
| Condenser Pressure (psia) | 115 | 115 | 115 | 115 |
| Bottom Pressure (psia) | 120 | 120 | 120 | 120 |
| Crude Feed Rate (pph) | 100 | 100 | 100 | 100 |
| Distillate Takeoff Rate (pph) | 10 | 10 | 10 | 20 |
| Bottoms Takeoff Rate (pph) | 91 | 91 | 91 | 81 |
| Reflux Rate (pph) | 50000 | 50000 | 22000 | 22000 |
| HCl Feed Rate (pph) | 1.00 | 1.00 | 1.00 | 1.00 |
| HCl in Distillate (pph) | 0.32 | 0.32 | 0.32 | 0.64 |
| HCl in Bottoms (pph) | 0.68 | 0.68 | 0.68 | 0.36 |

TABLE 3-continued

| | Case Number | | | |
|---|---|---|---|---|
| | 1 | 2 | 3 | 4 |
| Crude Feed To Column | | | | |
| $NF_3$ (ppmw) | 999000 | 999000 | 999900 | 999900 |
| PFC-14 (ppmw) | 1000 | 1000 | 100 | 100 |
| $NF_3$ (ppmm) | 999193 | 999193 | 999919 | 999919 |
| PFC-14 (ppmm) | 807 | 807 | 81 | 81 |
| Distillate (*) | | | | |
| PFC-14 (pph) | 0.09 | 0.10 | 0.01 | 0.01 |
| $NF_3$ (pph) | 9.59 | 9.58 | 9.67 | 19.35 |
| $NF_3$ in Feed That Is Lost Overhead (%) | 9.60 | 9.59 | 9.67 | 19.35 |
| $NF_3$ (ppmw) | 990461 | 989680 | 999054 | 999505 |
| PFC-14 (ppmw) | 9539 | 10320 | 946 | 495 |
| $NF_3$ (ppmm) | 992290 | 991657 | 999237 | 999601 |
| PFC-14 (ppmm) | 7710 | 8343 | 763 | 399 |
| Bottoms (*) | | | | |
| $NF_3$ (ppmw) | 999915 | 999999 | 999991 | 999995 |
| PFC-14 (ppmw) | 85 | 1.2 | 9.4 | 5 |
| $NF_3$ (ppmm) | 999931 | 999999 | 999992 | 999996 |
| PFC-14 (ppmm) | 69 | 1 | 7.6 | 4 |
| $NF_3$ Recovery Efficiency (%) | 90 | 90 | 90 | 80 |

* Concentrations (ppmw or ppmm) are on $NF_3$ + PFC-14 basis only (HCl is not included)

TABLE 4

| Case Number | 1 | 2 | 3 | 4 | 5 | 6 | 7 | 8 |
|---|---|---|---|---|---|---|---|---|
| Extractive Agent | PFC-218 | PFC-116 | CFC-13 | CFC-115 | HFC-125 | $CO_2$ | HFC-143a | HFC-23 |
| # of Stages | 120 | 120 | 120 | 120 | 120 | 120 | 120 | 120 |
| Extractive Agent Feed | 10 | 10 | 10 | 10 | 10 | 10 | 10 | 10 |
| Crude Feed | 20 | 20 | 20 | 20 | 20 | 70 | 20 | 20 |
| Column Top Temperature (° C.) | −82 | −82 | −82 | −82 | −82 | −63 | −82 | −82 |
| Reflux Temperature (° C.) | −82 | −82 | −82 | −82 | −82 | −63 | −82 | −82 |
| Distillate Temperature (° C.) | −82 | −82 | −82 | −82 | −82 | −63 | −82 | −82 |
| Bottoms Temperature (° C.) | 32 | −18 | −21 | 31 | 15 | −19 | 19 | −28 |
| Extractive Agent Feed Temperature (° C.) | −80 | −80 | −80 | −80 | −80 | −55 | −80 | −80 |
| Crude Feed Temperature (° C.) | −80 | −80 | −80 | −80 | −80 | −80 | −80 | −80 |
| Top Pressure (psia) | 165 | 165 | 165 | 165 | 165 | 318 | 165 | 165 |
| Condenser Pressure (psia) | 165 | 165 | 165 | 165 | 165 | 318 | 165 | 165 |

TABLE 4-continued

| | | | | | | | | |
|---|---|---|---|---|---|---|---|---|
| Bottoms Pressure (psia) | 168 | 168 | 168 | 168 | 168 | 321 | 168 | 168 |
| Distillate Takeoff Rate (pph) | 1.50 | 1.50 | 1.50 | 1.50 | 1.50 | 1.50 | 1.50 | 1.50 |
| Reflux Rate (pph) | 300 | 300 | 300 | 300 | 300 | 1000 | 300 | 300 |
| Bottoms Takeoff Rate (pph) | 18900.5 | 13899.7 | 10544.4 | 15545.2 | 12100.7 | 4499.5 | 8502.6 | 7099.9 |
| Extractive Agent Feed Rate (pph) | 18802.0 | 13801.2 | 10445.9 | 15446.7 | 12002.2 | 4401.0 | 8404.1 | 7001.4 |
| Crude Feed | | | | | | | | |
| $NF_3$ (pph) | 98.76 | 98.76 | 98.76 | 98.76 | 98.76 | 98.76 | 98.76 | 98.76 |
| PFC-14 (pph) | 1.24 | 1.24 | 1.24 | 1.24 | 1.24 | 1.24 | 1.24 | 1.24 |
| PFC-14 concentration in $NF_3$ feed (ppmm) | 10000 | 10000 | 10000 | 10000 | 10000 | 10000 | 10000 | 10000 |
| Distillate | | | | | | | | |
| $NF_3$ (pph) | 1.37 | 1.49 | 0.49 | 0.47 | 0.40 | 0.25 | 0.26 | 0.26 |
| PFC-14 (pph) | 0.127 | 0.0069 | 1.01 | 1.04 | 1.10 | 1.23 | 1.24 | 1.24 |
| Extractive Agent (pph) | <0.001 | <0.001 | <0.001 | <0.001 | <0.001 | 0.02 | <0.001 | <0.001 |
| Bottoms | | | | | | | | |
| $NF_3$ (pph) | 97.39 | 97.27 | 98.28 | 98.30 | 98.36 | 98.51 | 98.50 | 98.50 |
| PFC-14 (pph) | 1.11 | 1.23 | 0.22 | 0.20 | 0.14 | 0.01 | <0.001 | <0.001 |
| Extractive Agent (pph) | 18802.0 | 13801.2 | 10445.9 | 15446.7 | 12002.2 | 4401.0 | 8404.1 | 7001.4 |
| PFC-14 concentration in $NF_3$ (ppmw) | 11266 | 12488 | 2255 | 2044 | 1425 | 62.8 | 1.6 | 0.4 |
| PFC-14 concentration in $NF_3$ (ppmm) | 9110 | 10100 | 1820 | 1650 | 1150 | 50.7 | 1.3 | 0.3 |
| $NF_3$ Recovery Efficiency (%) | 98.6 | 98.5 | 99.5 | 99.5 | 99.6 | 99.7 | 99.7 | 99.7 |

| Case Number | 9 | 10 | 11 | 12 | 13 | 14 | 15 | 16 |
|---|---|---|---|---|---|---|---|---|
| Extractive Agent | $N_2O$ | $C_2H_6$ | HFC-41 | HCl | HCC-40 | HCFC-22 | HFC-32 | HFC-161 |
| # of Stages | 120 | 120 | 120 | 120 | 120 | 120 | 120 | 120 |
| Extractive Agent Feed Stage | 10 | 10 | 10 | 10 | 10 | 10 | 10 | 10 |
| Crude Feed Stage | 20 | 20 | 20 | 20 | 60 | 20 | 20 | 20 |
| Column Top Temperature (° C.) | −82 | −82 | −82 | −83 | −82 | −82 | −82 | −82 |
| Reflux Temperature (° C.) | −82 | −82 | −82 | −83 | −82 | −82 | −82 | −82 |
| Distillate Temperature (° C.) | −82 | −82 | −82 | −83 | −82 | −82 | −82 | −82 |
| Bottoms Temperature (° C.) | −39 | −36 | −32 | −65 | −75 | −8 | −50 | −64 |
| Extractive Agent Feed Temperature (° C.) | −80 | −80 | −80 | −80 | −80 | −80 | −80 | −80 |
| Crude Feed Temperature (° C.) | −80 | −80 | −80 | −80 | −80 | −80 | −80 | −80 |
| Top Pressure (psia) | 165 | 165 | 165 | 165 | 165 | 165 | 165 | 165 |
| Condenser Pressure (psia) | 165 | 165 | 165 | 165 | 165 | 165 | 165 | 165 |
| Bottoms Pressure (psia) | 168 | 168 | 168 | 168 | 168 | 168 | 168 | 168 |

TABLE 4-continued

| | | | | | | | | |
|---|---|---|---|---|---|---|---|---|
| Distillate Takeoff Rate (pph) | 1.50 | 1.50 | 1.50 | 2.00 | 1.50 | 1.50 | 1.50 | 1.50 |
| Reflux Rate (pph) | 300 | 300 | 300 | 300 | 300 | 300 | 300 | 300 |
| Bottoms Takeoff Rate (pph) | 2198.2 | 1052.2 | 1048.8 | 940.2 | 1083.8 | 1774.0 | 782.7 | 388.1 |
| Extractive Agent Feed Rate (pph) | 2099.7 | 953.7 | 950.3 | 842.2 | 985.3 | 1675.5 | 684.2 | 289.6 |
| Crude Feed | | | | | | | | |
| $NF_3$ (pph) | 98.76 | 98.76 | 98.76 | 98.76 | 98.76 | 98.76 | 98.76 | 98.76 |
| PFC-14 (pph) | 1.24 | 1.24 | 1.24 | 1.24 | 1.24 | 1.24 | 1.24 | 1.24 |
| PFC-14 concentration in $NF_3$ feed (ppmm) | 10000 | 10000 | 10000 | 10000 | 10000 | 10000 | 10000 | 10000 |
| Distillate | | | | | | | | |
| $NF_3$ (pph) | 0.26 | 0.26 | 0.25 | 0.69 | 0.26 | 0.26 | 0.26 | 0.26 |
| PFC-14 (pph) | 1.24 | 1.24 | 1.24 | 1.24 | 1.24 | 1.24 | 1.24 | 1.24 |
| Extractive Agent (pph) | <0.01 | <0.01 | 0.01 | 0.07 | <0.001 | <0.001 | <0.001 | <0.001 |
| Bottoms | | | | | | | | |
| $NF_3$ (pph) | 98.50 | 98.50 | 98.51 | 98.07 | 98.50 | 98.50 | 98.50 | 98.50 |
| PFC-14 (pph) | <0.001 | <0.001 | <0.001 | <0.001 | <0.001 | <0.001 | <0.001 | <0.001 |
| Extractive Agent (pph) | 2099.7 | 953.7 | 950.3 | 842.1 | 985.3 | 1675.5 | 684.2 | 289.6 |
| PFC-14 concentration in $NF_3$ (ppmw) | <0.13 | <0.13 | <0.13 | <0.13 | <0.13 | <0.13 | <0.13 | <0.13 |
| PFC-14 concentration in $NF_3$ (ppmm) | 0.1 | 0.1 | 0.1 | 0.1 | 0.1 | 0.1 | 0.1 | 0.1 |
| $NF_3$ Recovery Efficiency % | 99.7 | 99.7 | 99.7 | 99.3 | 99.7 | 99.7 | 99.7 | 99.7 |

TABLE 5

| | Case Number | | | |
|---|---|---|---|---|
| | 1 | 2 | 3 | 4 |
| Extractive Agent | $N_2O$ | HFC-32 | HCFC-22 | HFC-161 |
| # of Stages | 120 | 120 | 120 | 120 |
| Extractive Agent Feed Stage | 42 | 25 | 15 | 15 |
| Crude Feed Stage | 90 | 90 | 90 | 90 |
| Column Top Temperature (° C.) | −82 | −82 | −82 | −82 |
| Reflux Temperature (° C.) | −82 | −82 | −82 | −82 |
| Distillate Temperature (° C.) | −82 | −82 | −82 | −82 |
| Bottom Temperature (° C.) | −34 | 10 | 28 | 31 |
| Extractive Agent Feed Temperature (° C.) | −80 | −80 | −80 | −80 |
| Crude Stream Feed Temperature (° C.) | −80 | −80 | −80 | −80 |
| Column Top Pressure (psia) | 165 | 165 | 165 | 165 |
| Condenser Pressure (psia) | 165 | 165 | 165 | 165 |
| Bottom Pressure (psia) | 168 | 168 | 168 | 168 |
| Distillate Takeoff Rate (pph) | 98.5 | 98.5 | 98.5 | 98.5 |
| Reflux Rate (pph) | 1500.0 | 500.0 | 300.0 | 300.0 |
| Bottoms Takeoff Rate | 2156.5 | 776.4 | 1279.9 | 364.5 |
| Extractive Agent Feed Rate (pph) | 2155.0 | 774.9 | 1278.4 | 363.0 |
| Crude Feed Stream | | | | |
| PFC-14 (pph) | 99.19 | 99.19 | 99.19 | 99.19 |
| $NF_3$ (pph) | 0.81 | 0.81 | 0.81 | 0.81 |

TABLE 5-continued

| | Case Number | | | |
|---|---|---|---|---|
| | 1 | 2 | 3 | 4 |
| NF₃ concentration in PFC-14 Feed (ppmm) | 10000 | 10000 | 10000 | 10000 |
| Distillate | | | | |
| PFC-14 (pph) | 98.50 | 98.50 | 98.50 | 98.50 |
| NF₃ (pph) | <0.001 | <0.001 | <0.001 | <0.001 |
| Extractive Agent (pph) | <0.001 | <0.001 | <0.001 | <0.001 |
| PFC-14 concentration in distillate (Mole %) | 99.99998 | 99.99999 | 99.99999 | 99.99999 |
| NF₃ concentration in distillate (ppmm) | 0.10 | 0.10 | 0.10 | 0.10 |
| Extractive Agent concentration in distillate (ppmm) | <0.1 | <0.001 | <0.001 | <0.001 |
| PFC-14 Recovery Efficiency (%) | 99.3 | 99.3 | 99.3 | 99.3 |
| Bottoms | | | | |
| PFC-14 (pph) | 0.69 | 0.69 | 0.69 | 0.69 |
| NF₃ (pph) | 0.81 | 0.81 | 0.81 | 0.81 |
| Extractive Agent (pph) | 2155.0 | 774.9 | 1278.4 | 363.0 |

TABLE 6

| | Case Number | | | |
|---|---|---|---|---|
| | 1 | 2 | 3 | 4 |
| Extractive Agent | N₂O | HCFC-22 | N₂O | HCFC-22 |
| # of Stages | 120 | 120 | 120 | 120 |
| Extractive Agent Feed Stage | 15 | 10 | 42 | 15 |
| Crude Feed Stage | 25 | 20 | 90 | 90 |
| Top Temperature (° C.) | -82 | -82 | -82 | -82 |
| Reflux Temperature (° C.) | -82 | -82 | -82 | -82 |
| Distillate Temperature (° C.) | -82 | -82 | -82 | -82 |
| Bottoms Temperature (° C.) | -38 | 9 | -35 | 2 |
| Extractive Agent Feed Temperature (° C.) | -80 | -80 | -80 | -80 |
| Crude Feed Temperature (° C.) | -80 | -80 | -80 | -80 |
| Top Pressure (psia) | 165 | 165 | 165 | 165 |
| Condenser Pressure (psia) | 165 | 165 | 165 | 165 |
| Bottoms Pressure (psia) | 168 | 168 | 168 | 168 |

TABLE 6-continued

| | Case Number | | | |
|---|---|---|---|---|
| | 1 | 2 | 3 | 4 |
| Distillate Takeoff Rate (pph) | 57 | 57 | 54 | 54 |
| Reflux Rate (pph) | 600 | 300 | 1500 | 300 |
| Bottoms Takeoff Rate (pph) | 1273 | 1503 | 4489 | 1176 |
| Extractive Agent Feed Rate (pph) | 1230 | 1460 | 4443 | 1130 |
| Crude Feed | | | | |
| NF₃ (pph) | 44.7 | 44.7 | 44.7 | 44.7 |
| PFC-14 (pph) | 55.3 | 55.3 | 55.3 | 55.3 |
| PFC-14 concentration in NF₃ Feed (ppmm) | 500000 | 500000 | | |
| NF₃ concentration in PFC-14 Feed (ppmm) | | | 500000 | 500000 |
| Distillate | | | | |
| NF₃ (pph) | 1.63 | 1.65 | <0.001 | <0.001 |
| PFC-14 (pph) | 55.3 | 55.3 | 54.0 | 54.0 |
| Extractive Agent (pph) | <0.1 | <0.001 | <0.001 | <0.001 |
| Concentration of NF₃ in Distillate (ppmm) | | | 0.1 | 0.1 |
| Concentration of Extractive Agent in Distillate (ppmm) | | | <0.1 | <0.001 |
| Recovery Efficiency of PFC-14 (%) | | | 97.6 | 97.6 |
| Bottoms | | | | |
| NF₃ (pph) | 43.0 | 43.0 | 44.7 | 44.7 |
| PFC-14 (pph) | <0.001 | <0.001 | 1.35 | 1.35 |
| Extractive Agent (pph) | 1230 | 1460 | 4443 | 1130 |
| Concentration of PFC-14 in NF₃ (ppmm) | 0.1 | 0.1 | | |
| Recovery Efficiency of NF₃ (%) | 96.2 | 96.2 | | |

TABLE 7

| | Case Number | | | |
|---|---|---|---|---|
| | 1 | 2 | 3 | 4 |
| # of stages | 195 | 195 | 195 | 195 |
| Crude Feed Stage | 100 | 100 | 100 | 100 |
| Top Temperature (° C.) | -82 | -82 | -82 | -82 |
| Reflux Temperature (° C.) | -82 | -82 | -82 | -82 |
| Distillate Temperature (° C.) | -82 | -82 | -82 | -82 |
| Bottoms Temperature (° C.) | -82 | -82 | -82 | -82 |
| Crude Feed Temperature (° C.) | -80 | -80 | -80 | -80 |

TABLE 7-continued

| | Case Number | | | |
|---|---|---|---|---|
| | 1 | 2 | 3 | 4 |
| Top Pressure (psia) | 165 | 165 | 165 | 165 |
| Condenser Pressure (psia) | 165 | 165 | 165 | 165 |
| Bottoms Pressure (psia) | 168 | 168 | 168 | 168 |
| Distillate Takeoff Rate (pph) | 1.5 | 15 | 1.5 | 15 |
| Reflux Rate (pph) | 3430 | 3313 | 34952 | 33207 |
| Bottoms Takeoff Rate (pph) | 98.5 | 85 | 98.5 | 85 |
| Condenser Duty (pcu/hr) | −97500 | −97500 | −975000 | −975000 |
| Reboiler Duty (pcu/hr) | 97495 | 97892 | 974995 | 975391 |
| Crude Feed Stream | | | | |
| $NF_3$ (pph) | 98.76 | 98.76 | 98.76 | 98.76 |
| PFC-14 (pph) | 1.24 | 1.24 | 1.24 | 1.24 |
| PFC-14 concentration in $NF_3$ Feed (ppmm) | 10000 | 10000 | 10000 | 10000 |
| Distillate | | | | |
| $NF_3$ (pph) | 1.15 | 13.97 | 1.03 | 13.79 |
| PFC-14 (pph) | 0.35 | 1.03 | 0.47 | 1.21 |
| Bottoms | | | | |
| $NF_3$ (pph) | 97.61 | 84.79 | 97.74 | 84.97 |
| PFC-14 (pph) | 0.89 | 0.21 | 0.76 | 0.03 |
| PFC-14 Concentration in $NF_3$ (ppmm) | 7298 | 1969 | 6253 | 287 |
| $NF_3$ Recovery Efficiency (%) | 98.8 | 85.9 | 99.0 | 86.0 |

TABLE 8

| Operation | Case Number 5 |
|---|---|
| | Extraction Column |
| # of Stages | 120 |
| $N_2O$ Extractive Agent Feed Stage | 10 |
| Crude Feed Stage | 20 |
| Top Temperature (° C.) | −82 |
| Reflux Temperature (° C.) | −82 |
| Distillate Temperature (° C.) | −82 |
| Bottoms Temperature (° C.) | −39 |
| Extractive Agent Feed Temperature (° C.) | −80 |
| Crude Feed Temperature (° C.) | −80 |
| Top Pressure (psia) | 165 |
| Condenser Pressure (psia) | 165 |
| Bottoms Pressure (psia) | 168 |
| Distillate Rate (pph) | 1.5 |
| Reflux Rate (pph) | 300 |
| Bottoms Rate (pph) | 2203.7 |
| Extractive Agent Rate (pph) | 2105.2 |
| Condenser Duty (pcu/hr) | −7415 |
| Reboiler Duty (pcu/hr) | 46133 |
| Feed Cooler Duty (pcu/hr) | −42287 |
| Crude Feed Stream | |
| $NF_3$ (pph) | 98.76 |
| PFC-14 (pph) | 1.24 |
| Extractive Agent (pph) | 0.0 |
| PFC-14 concentration in $NF_3$ Feed (ppmm) | 10000 |
| Distillate | |
| $NF_3$ (pph) | 0.26 |
| PFC-14 (pph) | 1.24 |
| Extractive Agent (pph) | <0.01 |
| Bottoms | |
| $NF_3$ (pph) | 98.7 |
| PFC-14 (pph) | <0.001 |
| Extractive Agent (pph) | 2105 |
| PFC-14 Concentration in $NF_3$ (ppmm) | 0.1 |
| | Stripping Column |
| # of Stages | 75 |
| Extractive Agent/$NF_3$ Feed Stage | 46 |
| Top Temperature (° C.) | −82 |
| Reflux Temperature (° C.) | −82 |
| Distillate Temperature (° C.) | −82 |
| Bottoms Temperature (° C.) | −34 |
| Extractive Agent/$NF_3$ Feed Temperature (° C.) | −38 |
| Top Pressure (psia) | 165 |
| Condenser Pressure (psia) | 165 |
| Bottoms Pressure (psia) | 167 |
| Distillate Rate (pph) | 98.5 |
| Reflux Rate (pph) | 1600 |
| Bottoms Rate (pph) | 2105.2 |
| Condenser Duty (pcu/hr) | −47752 |
| Reboiler Duty (pcu/hr) | 52592 |
| Extractive Agent/$NF_3$ Feed Stream | |
| $NF_3$ (pph) | 98.7 |
| PFC-14 (pph) | <0.001 |
| Extractive Agent (pph) | 2105 |
| Distillate ($NF_3$ Product) | |
| $NF_3$ (pph) | 98.5 |
| PFC-14 (pph) | <0.001 |
| Extractive Agent (pph) | <0.001 |
| Combined PFC-14 + Extractive Agent concentration in $NF_3$ Distillate Product (ppmm) | 0.1 |
| Overall $NF_3$ Recovery Efficiency (%) | 99.7 |
| Bottoms | |
| $NF_3$ (pph) | 0.20 |
| PFC-14 (pph) | <0.001 |
| Extractive Agent (pph) | 2105 |

TABLE 9

| Operation | Case Number 1 |
|---|---|
| | Extraction Column |
| # of Stages | 120 |
| HCl Extractive Agent Feed Stage | 10 |
| Crude Feed Stage | 20 |
| Top Temperature (° C.) | −83 |
| Reflux Temperature (° C.) | −83 |

TABLE 9-continued

| | Case Number 1 |
|---|---|
| Distillate Temperature (° C.) | −83 |
| Bottoms Temperature (° C.) | −65 |
| Extractive Agent Feed Temperature (° C.) | −80 |
| Crude Feed Temperature (° C.) | −80 |
| Top Pressure (psia) | 165 |
| Condenser Pressure (psia) | 165 |
| Bottoms Pressure (psia) | 168 |
| Distillate Rate (pph) | 2.0 |
| Reflux Rate (pph) | 300 |
| Bottoms Rate (pph) | 939.7 |
| Extractive Agent Rate (pph) | 841.7 |
| Condenser Duty (pcu/hr) | −8602 |
| Reboiler Duty (pcu/hr) | 14431 |
| Feed Cooler Duty (pcu/hr) | −19494 |
| Crude Feed Stream | |
| $NF_3$ (pph) | 98.76 |
| PFC-14 (pph) | 1.24 |
| Extractive Agent (pph) | 0.0 |
| PFC-14 concentration in $NF_3$ Feed (ppmm) | 10000 |
| Distillate | |
| $NF_3$ (pph) | 0.69 |
| PFC-14 (pph) | 1.24 |
| Extractive Agent (pph) | 0.07 |
| Bottoms | |
| $NF_3$ (pph) | 98.1 |
| PFC-14 (pph) | <0.001 |
| Extractive Agent (pph) | 841.6 |
| PFC-14 Concentration $NF_3$ (ppmm) | 0.1 |

| Operation | Stripping Column |
|---|---|
| # of Stages | 32 |
| Extractive Agent/$NF_3$ Feed Stage | 16 |
| Top Temperature (° C.) | −83 |
| Reflux Temperature (° C.) | −83 |
| Distillate Temperature (° C.) | −83 |
| Bottoms Temperature (° C.) | −28 |
| Extractive Agent/$NF_3$ Feed Temperature (° C.) | −64 |
| Top Pressure (psia) | 165 |
| Condenser Pressure (psia) | 165 |
| Bottoms Pressure (psia) | 167 |
| Distillate Rate (pph) | 101.8 |
| Reflux Rate (pph) | 400 |
| Bottoms Rate (pph) | 837.9 |
| Condenser Duty (pcu/hr) | −13101 |
| Reboiler Duty (pcu/hr) | 29289 |
| Extractive Agent/$NF_3$ Feed Stream | |
| $NF_3$ (pph) | 98.1 |
| PFC-14 (pph) | <0.001 |
| Extractive Agent (pph) | 841.6 |
| Distillate ($NF_3$ Product) | |
| $NF_3$ (pph) | 98.1 |
| PFC-14 (pph) | <0.001 |
| Extractive Agent (pph) | 3.8 |
| PFC-14 concentration versus $NF_3$ in Distillate (ppmm) | 0.1 |
| Overall $NF_3$ Recovery Efficiency (%) | 99.3 |
| Bottoms | |
| $NF_3$ (pph) | <0.001 |
| PFC-14 (pph) | <0.001 |
| Extractive Agent (pph) | 837.9 |

What is claimed is:

1. A process for separating tetrafluoromethane (PFC-14) from nitrogen trifluoride ($NF_3$) comprising distilling a mixture comprising nitrogen trifluoride ($NF_3$) and tetrafluoromethane (PFC-14) in the presence of an entraining agent.

2. The process of claim 1 wherein the volatility of said tetrafluoromethane (PFC-14) or said nitrogen trifluoride ($NF_3$) is increased, one relative to the other, in the presence of said entraining agent.

3. The process of claim 1, comprising:
  a.) contacting said mixture comprising nitrogen trifluoride ($NF_3$) and tetrafluoromethane (PFC-14) with said entraining agent to form a second mixture, and
  b.) distilling said second mixture, and
  c.) recovering tetrafluoromethane (PFC-14) as a distillation column overhead stream, and entraining agent and nitrogen trifluotide ($NF_3$) as a distillation column bottom stream.

4. The process of claim 3 wherein said mixture comprising nitrogen trifluoride ($NF_3$) and tetrafluoromethane (PFC-14) is an azeotropic or azeotrope-like composition of nitrogen trifluoride ($NF_3$) and tetrafluoromethane (PFC-14) consisting essentially of from about 20 to about 55 mole percent tetrafluoromethane (PFC-14) and from about 80 to about 45 mole percent nitrogen trifluoride ($NF_3$), said composition having a boiling point from about −110° C. at 47 psia to about −40° C. at 645 psia.

5. The process of claim 3 wherein said entraining agent is an azeotropic or azeotrope-like composition consisting essentially of from 95 to 90 mole percent nitrous oxide ($N_2O$) and from 5 to 10 mole percent trifluoromethane (HFC-23), said composition having a boiling point from −90° C. at 13 psia to 25° C. at 824 psia.

6. The process of claim 3 wherein said entraining agent is an azeotropic or azeotrope-like composition consisting essentially of from 76 to 83 mole percent nitrous oxide ($N_2O$) and from 24 to 17 mole percent hydrogen chloride (HCl), said composition having a boiling point from −90 ° C. at 14 psia to 25 ° C. at 828 psia.

7. The process of claim 3 wherein said entraining agent is selected from the group consisting of hydrocarbons, hydrofluorocarbons, hydrochlorofluorocarbons, hydrochlorocarbons, hydrogen chloride, and oxides, wherein said oxides are selected from the group consisting of organic and inorganic oxides having a normal boiling point of from about −110 ° C. to about −25 ° C.

8. The process of claim 7 wherein:
  the hydrocarbons are selected from the group consisting of ethane, ethylene, propane, and propylene;
  the hydrofluorocarbons are selected from methyl fluoride (HFC-41), difluoromethane (HFC-32), 1, 1, 1-trifluoroethane (HFC-143a), *pentafluoroethane (HFC*-125), and fluoroethane (HFC-161);
  the hydrochlorofluorocarbon is chlorodifluoromethane (HCFC-22);

the hydrochlorocarbon is methyl chloride (HCC-40); and the oxides are selected from the group consisting of carbon dioxide ($CO_2$) and nitrous oxide ($N_2O$).

9. The process of claim 1 wherein said mixture comprising tetrafluoromethane (PFC-14) and nitrogen trifluoride ($NF_3$) is separated by:

contacting said mixture with hydrogen chloride (HCl) as entraining agent to form a second mixture, distilling said second mixture, and recovering an azeotropic or azeotropic or azeotrope-like composition of hydrogen chloride (HCl) and tetrafluoromethane (PFC-14) as a distillation column overhead stream, and substantially pure nitrogen trifluoride ($NF_3$) as a distillation column bottom stream, wherein said azeotropic or azeotrope-like composition consists essentially of from about 7 to about 9 mole percent hydrogen chloride (HCl) and from about 93 to about 91 mole percent tetrafluoromethane (PFC-14), said composition having a boiling point from about $-100°$ C. at 77 psia to about $-50°$ C. at 497 psia.

10. The process of claims 1 or 3 wherein nitrogen trifluoride ($NF_3$) or tetrafluoromethane (PFC-14) is recovered substantially free of impurities.

11. The process of claim 1 or 3 wherein nitrogen trifluoride ($NF_3$) is recovered containing less than about 10 parts-per-million-molar impurities.

12. The process of claim 1 or 3 wherein said nitrogen trifluoride ($NF_3$) is recovered substantially free of tetrafluoromethane (PFC-14).

13. The process of claim 12 wherein said nitrogen trifluoride ($NF_3$) is recovered containing less than 10 parts-per-million-molar tetrafluoromethane (PFC-14).

14. The process of claim 12 wherein said nitrogen trifluoride ($NF_3$) is recovered containing less than 3 parts-per-million-molar tetrafluoromethane (PFC-14).

15. The process of claim 12 wherein said nitrogen trifluoride ($NF_3$) is recovered containing less than 1 parts-per-million-molar tetrafluoromethane (PFC-14).

16. A process for separating a fluorocompound selected from the group consisting of tetrafluoromethane (PFC-14) and nitrogen trifluoride ($NF_3$) from a first mixture of said fluorocompound and other compounds, comprising:

contacting the first mixture with hydrogen chloride (HCl) entraining agent to form a second mixture, distilling the second mixture to form an azeotropic or azeotrope-like composition of said fluorocompound and hydrogen chloride (HCl), and recovering said azeotropic or azeotrope-like composition of said fluorocompound and hydrogen chloride (HCl) in a distillation column overhead stream, and said other compounds in a distillation column bottom stream.

17. The process of claim 16 wherein said fluorocompound is nitrogen trifluoride ($NF_3$) and said azeotropic or azeotrope-like composition consists essentially of from 94 to 93 mole percent nitrogen trifluoride ($NF_3$) and from 6 to 7 mole percent hydrogen chloride (HCl), said composition having a boiling point from $-100°$ C. at 79 psia to $-50°$ C. at 487 psia.

18. The process of claim 16 wherein said other compounds are selected from the group consisting of hexafluoroethane (PFC-116), octafluoropropane (PFC-218), carbon dioxide ($CO_2$), sulfur hexafluoride ($SF_6$), nitrous oxide ($N_2O$), ethane ($C_2H_6$), and tetrafluoroethylene ($C_2F_4$).

19. The process of claim 16 wherein said fluorocompound is recovered substantially free of said other compounds.

20. The process of claim 16 wherein said nitrogen trifluoride ($NF_3$) is recovered containing less than 10 parts-per-million-molar of said other compounds.

21. A process for separating nitrogen trifluoride ($NF_3$) from a first mixture of nitrogen trifluoride ($NF_3$) and tetrafluoromethane (PFC-14) wherein the amount of nitrogen trifluoride ($NF_3$) in the first mixture is in excess of the amount of nitrogen trifluoride ($NF_3$) in an azeotropic or azeotrope-like composition of nitrogen trifluoride ($NF_3$) and tetrafluoromethane (PFC-14), comprising:

a.) distilling the first mixture to form an azeotropic or azeotrope-like composition of nitrogen trifluoride ($NF_3$) and tetrafluoromethane (PFC-14) as a second mixture, and b.) recovering the second mixture as a distillation column overhead stream, and nitrogen trifluoride ($NF_3$) as a distillation column bottom stream.

22. A process for separating tetrafluoromethane (PFC-14) from a first mixture of nitrogen trifluoride ($NF_3$) and tetrafluoromethane (PFC-14) wherein the amount of tetrafluoromethane (PFC-14) in the first mixture is in excess of the amount of tetrafluoromethane (PFC-14) in an azeotropic or azeotrope-like composition of nitrogen trifluoride ($NF_3$) and tetrafluoromethane (PFC-14), comprising:

distilling the first mixture to form an azeotropic or azeotrope-like composition comprising nitrogen trifluoride ($NF_3$) and tetrafluoromethane (PFC-14) as a second mixture, and recovering the second mixture as a distillation column overhead stream, and tetrafluoromethane (PFC-14) as a distillation column bottom stream.

23. The process of claims 21 or 22 wherein said azeotropic or azeotrope-like composition consists essentially of from 20 to 55 mole percent tetrafluoromethane (PFC-14) and from 80 to 45 mole percent nitrogen trifluoride ($NF_3$), said composition having a boiling point from $-110°$ C. at 47 psia to $-40°$ C. at 645 psia.

* * * * *